(12) United States Patent
Irisawa

(10) Patent No.: US 9,958,419 B2
(45) Date of Patent: May 1, 2018

(54) LIGHT SOURCE UNIT AND PHOTOACOUSTIC MEASUREMENT APPARATUS USING THE SAME

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 407 days.

(21) Appl. No.: 14/621,743

(22) Filed: Feb. 13, 2015

(65) Prior Publication Data

US 2015/0160168 A1 Jun. 11, 2015

Related U.S. Application Data

(63) Continuation of application No. PCT/JP2013/072134, filed on Aug. 20, 2013.

(30) Foreign Application Priority Data

Sep. 3, 2012 (JP) .................................. 2012-193061

(51) Int. Cl.
*A61B 5/00* (2006.01)
*F21V 13/02* (2006.01)
(Continued)

(52) U.S. Cl.
CPC ......... *G01N 29/223* (2013.01); *A61B 5/0095* (2013.01); *F21V 13/02* (2013.01);
(Continued)

(58) Field of Classification Search
CPC ... F21V 13/02; A61B 5/0095; G01N 21/1702; G01N 21/63; G01N 2021/1706; G01N 2201/084
See application file for complete search history.

(56) References Cited

U.S. PATENT DOCUMENTS

2010/0259917 A1* 10/2010 Ramer ..................... F21K 9/00
362/84

FOREIGN PATENT DOCUMENTS

JP 2007-307007 A 11/2007
JP 2007307007 A * 11/2007
(Continued)

OTHER PUBLICATIONS

Notice of Reasons for Rejections dated Oct. 20, 2015, issued in JP 2012-193061.
(Continued)

*Primary Examiner* — R. A Smith
*Assistant Examiner* — John M Royston
(74) *Attorney, Agent, or Firm* — Birch, Stewart, Kolasch & Birch, LLP

(57) ABSTRACT

It is desirable to more stably and efficiently transmit light in a housing of a light source unit. A light source unit 13, which emits a laser beam L to a light guide part 40, includes: a unit housing 13b that includes a connector receiving portion 51b detachably connected to a connector portion 51a; a light source 30 that is installed in the unit housing 13b and outputs the laser beam L; a diffusion part 80 that diffuses the laser beam L output from the light source 30; a condensing lens system 81 that condenses the laser beam L diffused by the diffusion part 80; and an optical fiber 82a that transmits the laser beam L, which is condensed by the condensing lens system 81, to the connector receiving portion 51b. The connector receiving portion 51b optically connects the optical fiber 82a to the light guide part 40.

5 Claims, 22 Drawing Sheets

(51) Int. Cl.

| | | |
|---|---|---|
| *G01N 21/17* | (2006.01) | |
| *G01N 29/22* | (2006.01) | |
| *G01N 21/63* | (2006.01) | |
| *F21V 8/00* | (2006.01) | |
| *G02B 6/42* | (2006.01) | |
| *G02B 6/36* | (2006.01) | |

(52) U.S. Cl.
CPC ......... *G01N 21/1702* (2013.01); *G01N 21/63* (2013.01); *G02B 6/0005* (2013.01); *G02B 6/4292* (2013.01); *G01N 2021/1706* (2013.01); *G01N 2201/084* (2013.01); *G02B 6/3624* (2013.01); *G02B 6/4206* (2013.01)

(56) References Cited

FOREIGN PATENT DOCUMENTS

| | | | | |
|---|---|---|---|---|
| JP | 2010-12295 A | | 1/2010 | |
| JP | 2012173136 A | * | 9/2012 | ........... G02B 6/4206 |
| WO | WO 2012/114709 A1 | | 8/2012 | |

OTHER PUBLICATIONS

International Search Report, issued in PCT/JP2013/072134, dated Oct. 8, 2013.
Written Opinion of the International Searching Authority, issued in PCT/JP2013/072134, dated Oct. 8, 2013.
Notice of Reasons for Rejection issued in corresponding Chinese Application No. 201380043184.3 dated Jan. 11, 2016, along with an English translation.

\* cited by examiner

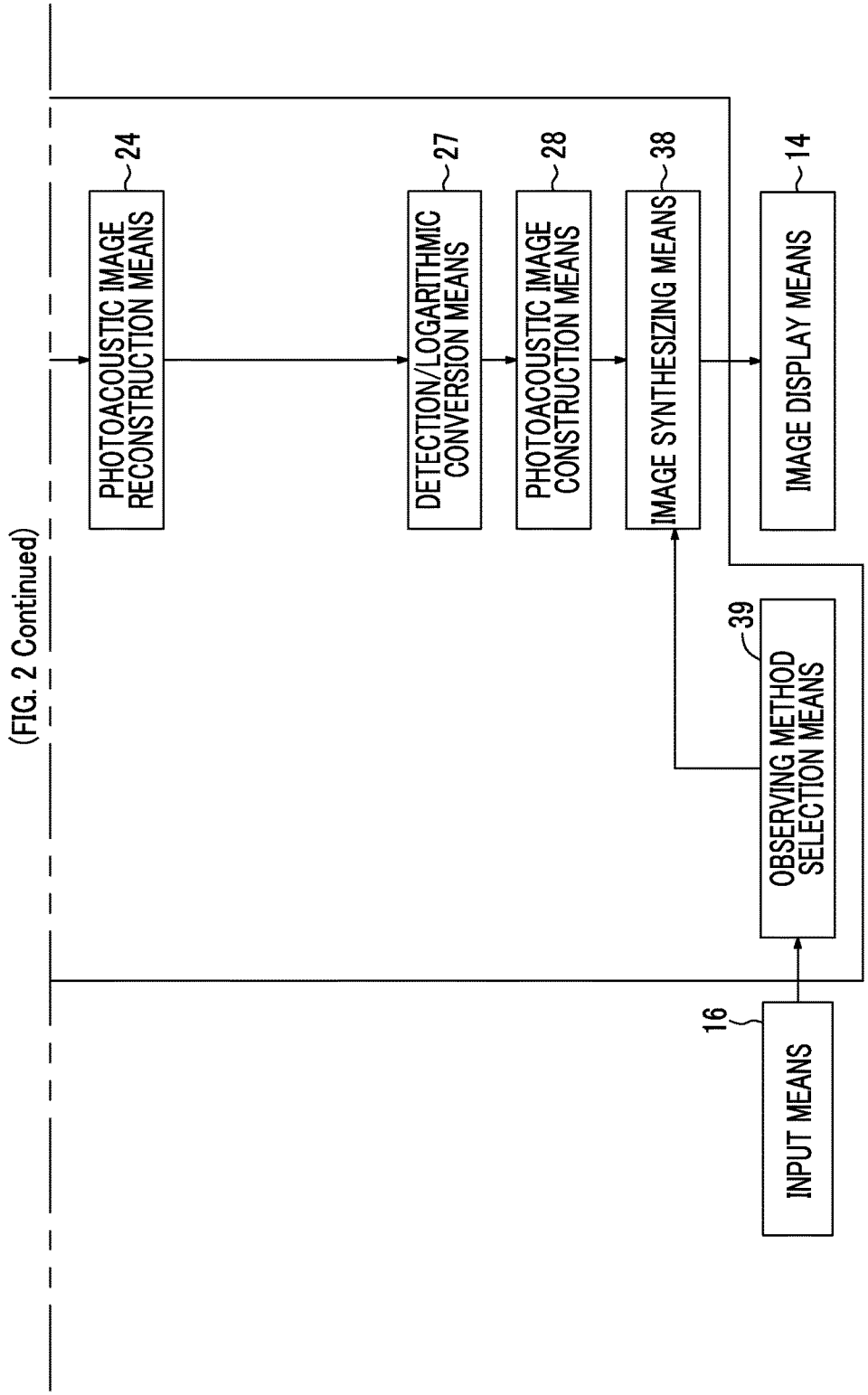

FIG. 10A
FIG. 10B
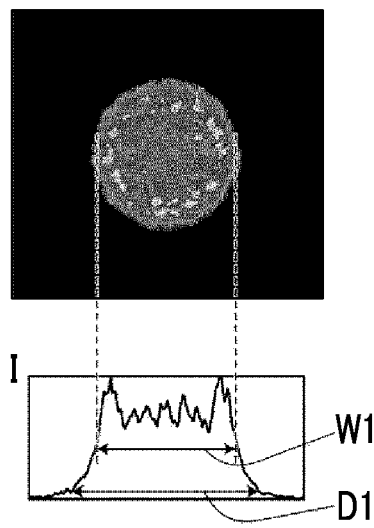
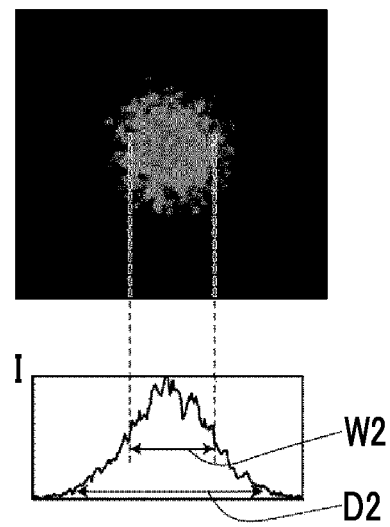

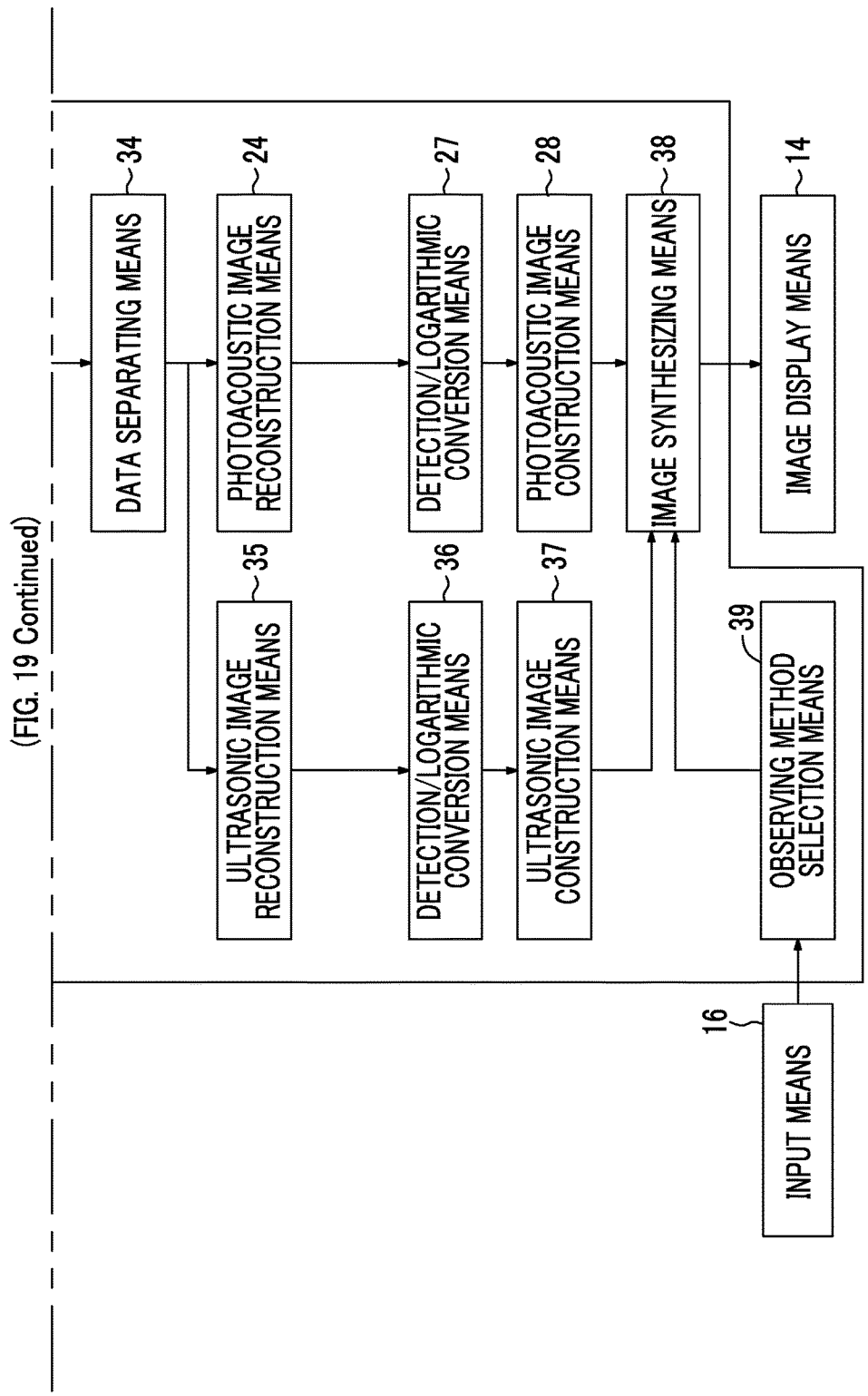

LIGHT SOURCE UNIT AND PHOTOACOUSTIC MEASUREMENT APPARATUS USING THE SAME

CROSS-REFERENCE TO RELATED APPLICATIONS

This application is a Continuation of PCT International Application No. PCT/JP2013/072134 filed on Aug. 20, 2013, which claims priority under 35 U.S.C § 119(a) to Japanese Patent Application No. 2012-193061 filed on Sep. 3, 2012. Each of the above applications is hereby expressly incorporated by reference, in its entirety, into the present application.

BACKGROUND OF THE INVENTION

1. Field of the Invention

The present invention relates to a light source unit that emits a laser beam and a photoacoustic measurement apparatus using the light source unit.

2. Description of the Related Art

Photoacoustic spectroscopy is a method that includes irradiating a subject with light having a predetermined wavelength (for example, the wavelength band of visible light, near infrared light, or middle infrared light) and detecting a photoacoustic wave, which is an elastic wave generated when a specific material contained in the subject absorbs the energy of this light, to measure the concentration or distribution of the specific material (for example, JP2010-12295A). The specific material contained in the subject is glucose, hemoglobin, or the like contained in blood when the subject is, for example, a human body. Further, a technique, which detects photoacoustic waves and generates a photoacoustic image on the basis of the detected signals, is called photoacoustic imaging (PAI) or photo-acoustic tomography (PAT).

Since the intensity of a laser beam, which is applied to the subject, is significantly attenuated due to absorption or scattering while the laser beam is propagated through the subject, a laser beam having high light energy is generally used in the measurement (photoacoustic measurement) using the photoacoustic spectroscopy. As shown in, for example, FIG. 20, a photoacoustic measurement apparatus 1 includes a probe 4 for photoacoustic measurement, a light source unit 3 that supplies a laser beam L to the probe 4, and an acoustic signal processing unit 2 that processes signals of the photoacoustic waves detected by the probe 4. Further, for convenience of use, the probe 4 and the acoustic signal processing unit 2 are detachably connected to each other by a first connector 5a, and the probe 4 and the light source unit 3 are detachably connected to each other by a second connector 5b. An acoustic detecting element array 4a is provided in the probe 4, and the acoustic detecting element array 4a is connected to control means 2a of the acoustic signal processing unit 2 by a control signal line 4c. A laser beam L output from a light source 3a is guided to an end of the probe 4 by an optical fiber 4b, and a subject M is irradiated with the laser beam L.

Incidentally, when the probe and the light source unit are detachably connected to each other as described above, space transmission is frequently used without a light guide member such as an optical fiber as the transmission of a laser beam in a housing of the light source unit. The reason for this is that an optical fiber cannot withstand light energy and is broken when a laser beam is transmitted using an optical fiber in the housing. For example, the transmission of a laser beam L between the light source 3a and the second connector 5b in the light source unit 3 of FIG. 20 is performed by space transmission.

SUMMARY OF THE INVENTION

However, when space transmission is employed as the transmission of a laser beam in the housing as described above, the inside of the housing of the light source unit and a housing wall move in different manners with a temperature change and vibration. Accordingly, the incident position of a laser beam, which is incident on a connector receiving portion, is shifted. For this reason, there are problems in that the amount of energy to be transmitted may not be stable and transmission efficiency may be lowered. In this case, there may be a case in which transmission efficiency is lower than the efficiency of light transmission using the light guide member.

The invention has been made in consideration of the above-mentioned problems, and an object of the invention is to provide a light source unit that can more stably and efficiently transmit light in a housing of the light source unit and a photoacoustic measurement apparatus using the light source unit.

In order to solve the above-mentioned problems, a light source unit, which emits a laser beam to a light guide part of a probe, according to the invention includes a unit housing having a connector receiving portion detachably connected to a connector portion of the light guide part, a light source that is installed in the unit housing and outputs the laser beam, a diffusion part that diffuses the laser beam output from the light source, a condensing lens system that condenses the laser beam diffused by the diffusion part, and a light transmitting part that includes an optical fiber transmitting the laser beam, which is condensed by the condensing lens system, to the connector receiving portion. The connector receiving portion optically connects the optical fiber to the light guide part.

Meanwhile, a photoacoustic measurement apparatus according to the invention includes a probe that has a light guide part guiding a laser beam emitted toward a subject to generate a photoacoustic wave, and the light source unit.

Further, in the light source unit and the photoacoustic measurement apparatus according to the invention, the optical fiber may be a single fiber.

Further, when the optical fiber is a single fiber, the light transmitting part may have a light energy resistant structure at a light incident-side end portion of the optical fiber, the condensing lens system may condense the laser beam so that a minimum beam diameter D of the laser beam defined by the following expression 1 is $d_{in}/2$ or more in a relationship between a diameter $d_{in}$ of a core of the optical fiber on a light incident side and the minimum beam diameter D, and a light incident-side end face of the core of the optical fiber may be disposed so that the laser beam is incident on the light incident-side end face of the core while the diameter of the laser beam is $d_{in}/2$ or more. In this case, the light transmitting part may be an air gap-optical fiber cable having a covering member that covers the optical fiber so that a side surface of the optical fiber adjacent to an end face of the optical fiber is exposed to the outside.

$$D = A \cdot f \cdot \tan\left(\sqrt{\left(\frac{\phi}{2}\right)^2 + \left(\frac{\theta}{2}\right)^2}\right) \quad \text{Expression 1}$$

In Expression 1, A denotes a coefficient that is determined depending on the kind of the diffusion part, f denotes a focal length of the condensing lens system, φ denotes a spread angle of the laser beam when the laser beam is incident on the diffusion part, and θ denotes a diffusion angle of the diffusion part.

The "spread angle" means an angle where the diameter of a laser beam is increased with the propagation of the laser beam. Further, the "diffusion angle" of the diffusion part means a design diffusion angle, that is, an angle where the diameter of a laser beam as parallel light incident on and transmitted through the diffusion part is increased with the propagation of the laser beam. Meanwhile, the "spread angle" and the "diffusion angle" are represented by a total plane angle. When these angles are to be measured, it is preferable that a beam diameter be measured at about 10 points within a range of a propagation distance until a certain beam diameter is increased to double the beam diameter and the angles be obtained from the inclination of the change of the beam diameter at this time.

Furthermore, the "beam diameter" is set to the diameter of a circle which includes about 86.5% energy and of which the center is positioned on a beam center (generally, a position where the intensity of a beam is the maximum) in the energy profile of the laser beam L, that is, a so-called $1/e^2$ diameter. In this case, when it is difficult to obtain a beam center due to the irregular distribution of the intensity of a beam, or the like, circles in which energy is 86.5% in the vicinity of a position that is estimated as the beam center are exhaustively made and the diameter of a circle having the minimum area among these circles may be used as the beam diameter.

Alternatively, when the optical fiber is a single fiber, the condensing lens system may condense the laser beam so that a minimum beam diameter D of the laser beam defined by Expression 1 is in the range of $d_{in}/3$ to $2d_{in}/3$ in a relationship between a diameter $d_{in}$ of a core of the optical fiber on a light incident side and the minimum beam diameter D, and a light incident-side end face of the core of the optical fiber may be disposed so that the laser beam is incident on the light incident-side end face of the core while the diameter of the laser beam is in the range of $d_{in}/3$ to $2d_{in}/3$.

Further, in the light source unit and the photoacoustic measurement apparatus according to the invention, the diffusion part may be a lens diffuser in which small lenses are randomly disposed on a surface of a substrate.

Furthermore, in the light source unit and the photoacoustic measurement apparatus according to the invention, the diffusion part may make a top of the energy profile of the incident laser beam flat.

Moreover, in the light source unit and the photoacoustic measurement apparatus according to the invention, the diffusion part may be an engineered diffuser and the coefficient A may be 2.5.

Further, in the light source unit and the photoacoustic measurement apparatus according to the invention, the diffusion part may be a holographic diffuser and the coefficient A may be 2.4.

Furthermore, in the photoacoustic measurement apparatus according to the invention, the light guide part may be a bundle fiber, and a diameter $d_{out}$ of the core of the optical fiber on a light-emitting side and a bundle diameter B of the bundle fiber may satisfy the following expression 2.

$$0.8B \leq d_{out} \leq 1.2B \qquad \text{Expression 2}$$

Moreover, in the light source unit and the photoacoustic measurement apparatus according to the invention, the connector receiving portion may hold the optical fiber so that a direction of a first optical axis of the optical fiber on a light-emitting side has an inclination.

In addition, when the direction of the first optical axis has an inclination, an insertion passage of the connector receiving portion into which an insertion portion of the connector portion is inserted may have a guide structure guiding the insertion portion with the insertion of the insertion portion so that a second optical axis of the light guide part on a light incident side corresponds to the first optical axis. In this case, in the guide structure, an opening width of the insertion passage may be larger than the width of an inner portion of the insertion passage and an inner wall surface of the insertion passage may be curved from an opening side toward an inner portion side. Further, the inner wall surface of the insertion passage may be provided with rollers.

The light source unit and the photoacoustic measurement apparatus according to the invention transmit light to the connector receiving portion in the housing by using the optical fiber. Accordingly, even though the inside of the housing and the housing wall move in different manners with a temperature change and vibration, it is possible to prevent the incident position of light, which is incident on the connector receiving portion, from being shifted. In addition, the light source unit and the photoacoustic measurement apparatus according to the invention increase the distribution of a propagation angle of light flux, which is included in a laser beam, by allowing the laser beam to pass through the diffuser once, and control a beam diameter of the laser beam incident on the optical fiber, by using the focal length of the condensing lens system. Accordingly, when condensing a laser beam by the condensing lens system and allowing the laser beam to be incident on the optical fiber, the light source unit and the photoacoustic measurement apparatus can prevent the laser beam from being excessively narrowed. Therefore, it is possible to prevent damage to the optical fiber that is caused when local light energy exceeds the damage threshold energy of the optical fiber. As a result, it is possible to more stably and efficiently transmit light in the housing of the light source unit.

Moreover, while a laser beam is transmitted through the optical fiber, the energy profile of the laser beam is made uniform. Accordingly, an effect of uniformly transmitting light to the light guide part of the probe is also obtained.

BRIEF DESCRIPTION OF THE DRAWINGS

FIG. 10A is a view showing the energy profile of a laser beam that is condensed by a lens after the top of the energy profile of the laser beam is made flat by an engineered diffuser, and FIG. 10B is a view showing the energy profile of a laser beam that is condensed by a lens after the laser beam is diffused by a holographic diffuser.

DESCRIPTION OF THE PREFERRED EMBODIMENTS

Figure 1:
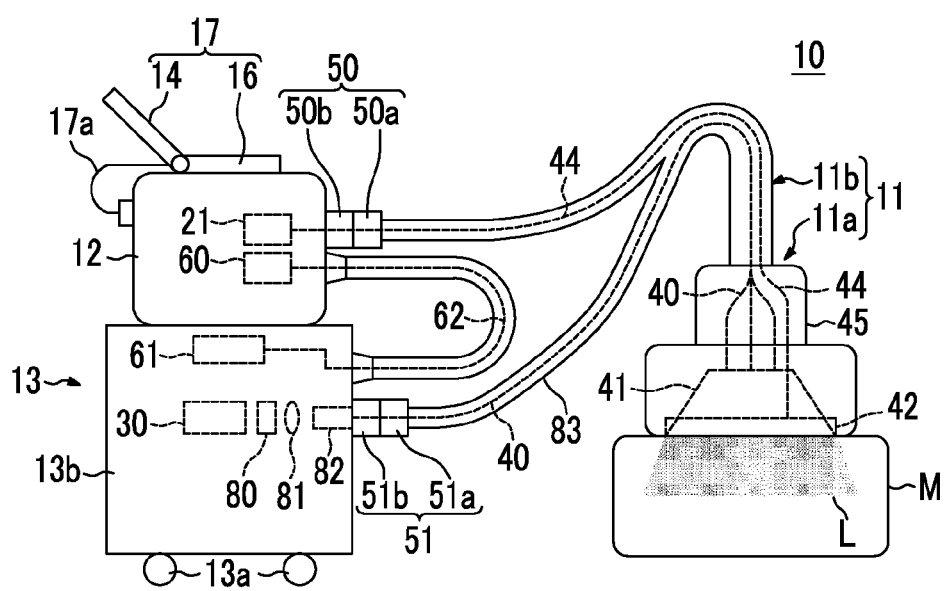
FIG. 1 is a schematic view showing the configuration of a photoacoustic measurement apparatus of a first embodiment.

Embodiments of the invention will be described below with reference to the drawings, but the invention is not limited thereto. Meanwhile, for the facilitation of visual recognition, the scale or the like of each component in the drawings may be appropriately different from the scale of an actual component.

[First Embodiment]

Figure 2:
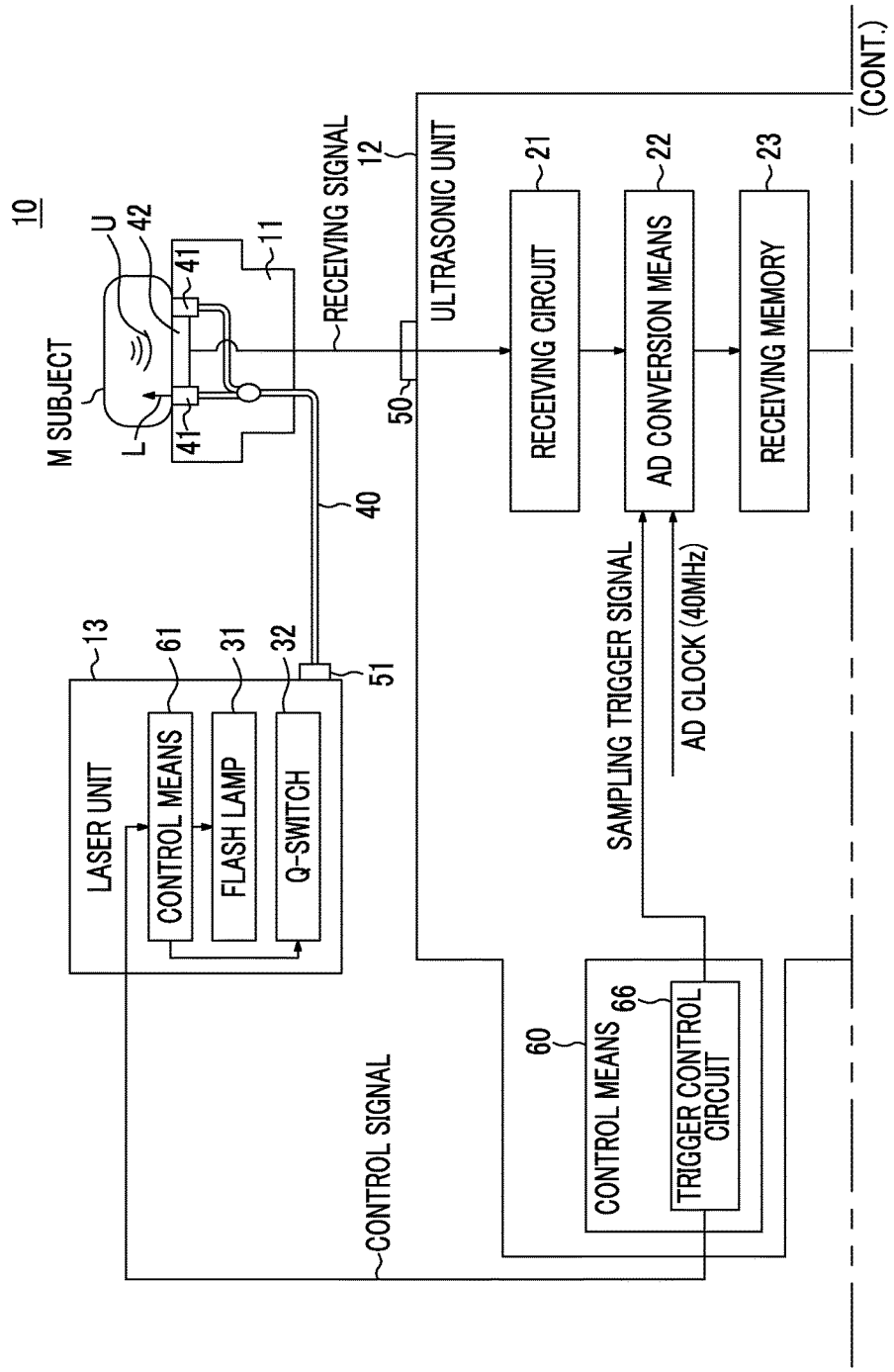
FIG. 2 is a block diagram showing the internal configuration of the photoacoustic measurement apparatus of the first embodiment.
Figure 3:
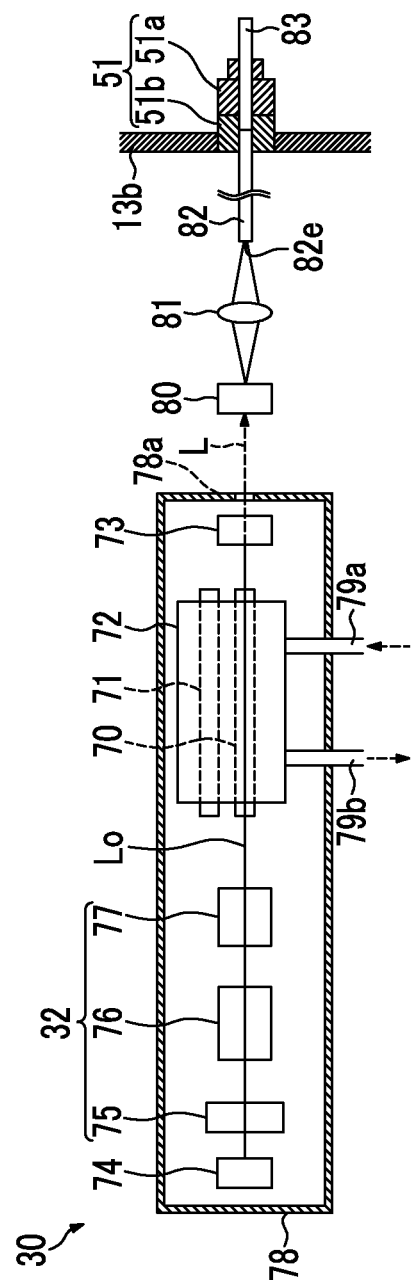
FIG. 3 is a schematic view showing the configuration of the inside of a unit housing.

FIG. 1 is a schematic view showing the configuration of a photoacoustic measurement apparatus of a first embodiment, and FIG. 2 is a block diagram showing the internal configuration of the photoacoustic measurement apparatus of the first embodiment. Further, FIG. 3 is a schematic view showing the configuration of a part of the inside of a unit housing. Meanwhile, in this embodiment, the photoacoustic measurement apparatus is a photoacoustic image forming apparatus that forms photoacoustic images on the basis of photoacoustic signals.

As shown in FIG. 1, the photoacoustic image forming apparatus 10 of this embodiment includes a probe 11, an ultrasonic unit 12, a laser unit 13, and a personal computer (PC) 17. Further, a subject M is irradiated with a beam L, which is emitted from the laser unit 13, through the probe 11 and a photoacoustic wave, which is caused by the irradiation with the beam, is detected by the probe 11.

<Probe>

As shown in FIGS. 1 and 2, the probe 11 is mainly divided into a probe main body 11a (a portion on which inherent functions of the probe are concentrated) and a cable portion 11b. Further, the probe main body 11a mainly includes light guide plates 41, an acoustic detector 42, and a housing 45 that houses the light guide plates 41 and the acoustic detector 42. Meanwhile, an optical fiber 40 and an acoustic signal line 44 are mainly inserted into the cable portion 11b. The probe 11 and the ultrasonic unit 12 are detachably connected to each other by a connector 50, and the probe 11 and the laser unit 13 are detachably connected to each other by a connector 51.

The optical fiber 40 is optically connected to the laser unit 13, which outputs a laser beam L, through the connector 51, and guides the laser beam L to the light guide plates 41. The optical fiber 40 corresponds to a light guide part of the invention. The optical fiber 40 is not particularly limited, and a known fiber, such as a quartz fiber, can be used as the optical fiber 40. A single fiber or a bundle fiber may be used as the optical fiber 40, but a bundle fiber is more preferable. Further, when the optical fiber 40 is a bundle fiber, it is preferable that the bundle fiber be a fused bundle fiber of which a light incident-side end portion is fused. In the fused bundle fiber, clads of optical fibers are fused to one another so that the optical fibers are bundled in a hexagonal honeycomb shape. Accordingly, a clearance between the optical fibers is reduced in comparison with bundling using an adhesive. For this reason, there is an advantage of increasing an area, which is occupied by the core, per unit area. Furthermore, since a material, which is weak against light energy, does not appear at the light incident-side end portion of the bundle fiber, there also is an advantage of improving durability against light energy.

The light guide plate 41 is a plate that is obtained by performing special processing on the surface of, for example, an acrylic plate or a quartz plate and uniformly emits light, which has been incident on one end face thereof, from the other end face thereof. For example, in this embodiment, two light guide plates 41 are disposed so as to face each other with the acoustic detector 42 interposed therebetween. The optical fiber 40 is optically connected to the light guide plates 41. For example, portions of the light guide plates 41 connected to the optical fiber 40 are formed in a tapered shape as shown in FIG. 1. Accordingly, an area to be irradiated with light can be widened.

The acoustic detector 42 detects an acoustic wave from a subject, and generates electric signals (acoustic signals) corresponding to the intensity of the detected acoustic wave. Meanwhile, in this specification, the "acoustic wave" means a wave that includes an ultrasonic wave and a photoacoustic wave. Here, the "ultrasonic wave" means an elastic wave, which is generated in a subject by the vibration of an acoustic wave generator such as a piezoelectric element, and the reflected wave thereof, and the "photoacoustic wave" means an elastic wave that is generated in a subject due to a photo-acoustic effect caused by the irradiation with light.

The acoustic detector 42 includes, for example, a backing material, an acoustic detecting element array, a control circuit for the acoustic detecting element array, an acoustic matching layer, and an acoustic lens. The acoustic detecting element array is an array in which a plurality of acoustic detecting elements are one-dimensionally or two-dimensionally arrayed, and converts an actually detected acoustic wave into an electric signal. The acoustic detecting element is a piezoelectric element that is formed of a film made of a polymer, such as piezoelectric ceramics or polyvinylidene fluoride (PVDF).

The acoustic signal line 44 is an electrical signal line that transmits acoustic signals generated by the acoustic detector 42 to the ultrasonic unit 12 or transmits signals transmitted from the ultrasonic unit 12 to the control circuit for the acoustic detecting element array.

<Ultrasonic Unit>

The ultrasonic unit 12 receives photoacoustic signals, which are transmitted from the probe 11, through the connector 50, and forms a photoacoustic image on the basis of the photoacoustic signals. The ultrasonic unit 12 and the laser unit 13 are connected to each other by a control signal line 62. The details of the ultrasonic unit 12 will be described below.

The connector 50 is a connecting member that electrically connects the acoustic signal line 44 to a receiving circuit 21 of the ultrasonic unit 12. For example, a known multi-core connector can be used as this connector. The connector 50 includes a plug 50a and a receptacle 50b that has a structure corresponding to the plug 50a and is detachably connected to the plug 50a.

The control signal line 62 is a signal line that connects control means 60 of the ultrasonic unit 12 to control means 61 of the laser unit 13, and is, for example, an electrical signal line. The ultrasonic unit 12 and the laser unit 13 can communicate with each other by transmitting and receiving a control signal through the control signal line 62. In this specification, the meaning of "transmitting and receiving" a control signal includes that a control signal is unidirectionally transmitted from one of the ultrasonic unit 12 and the laser unit 13 to the other thereof and both the units bidirectionally transmit or receive a control signal.

A control signal is, for example, a trigger signal that synchronizes an output timing of a laser beam with photoacoustic detection timing. The trigger signal may be a signal that is transmitted to the ultrasonic unit 12 by the laser unit 13, and may be a signal indicating the output of a laser beam (that is, a trigger signal in the setting where the laser unit is a superordinate). Alternatively, the trigger signal may be a signal that is transmitted to the laser unit 13 by the ultrasonic unit 12, and may be a signal instructing the output of a laser beam to be prepared or instructing a laser beam to be output (that is, a trigger signal in the setting where the ultrasonic unit is a superordinate).

<Laser Unit>

The laser unit 13 includes an oscillator 30 that oscillates a laser beam L, a diffusion part 80, a condensing lens system 81, an optical fiber cable 82, and a unit housing 13b that houses the oscillator 30, the diffusion part 80, the condensing lens system 81, and the optical fiber cable 82. The laser unit 13 emits a laser beam L as light with which the subject M is irradiated. The laser unit 13 corresponds to a light source unit of the invention. For example, the laser unit 13 is adapted to receive a trigger signal, which is transmitted from the control means 60 of the ultrasonic unit 12, and to emit a laser beam L. The laser beams L, which is emitted from the laser unit 13, is guided to the light guide plates 41 of the probe 11 by the light guide part such as the optical fiber 40. Casters 13a are provided on the bottom of the laser unit 13 so that the laser unit 13 can be easily moved. Further, the unit housing 13b includes a receptacle 51b that forms the connector 51.

In this embodiment, an optical system provided in the laser unit 13 is formed so that a laser beam L is incident on an end portion of the optical fiber 40 connected by the connector 51. That is, the laser beam L, which is incident on the diffusion part 80 after being output from the oscillator 30, is incident on a light incident-side end portion 82e of the optical fiber cable 82 through the condensing lens system 81. After that, the laser beam L, which is transmitted by using the optical fiber cable 82, is emitted to the optical fiber 40 of the probe 11 at the connector 51. The optical system will be described in detail below.

The structure of the oscillator 30 is not particularly limited. However, as shown in FIG. 3, the oscillator 30 includes a laser rod 70, an excitation lamp 71, a laser chamber 72, an output mirror 73, a total reflection mirror 74, a Q-switch 32, and a housing 78 that houses the laser rod 70, the excitation lamp 71, the laser chamber 72, the output mirror 73, the total reflection mirror 74, and the Q-switch 32. In this embodiment, the oscillator 30 corresponds to a light source of the invention. The laser rod 70 is a solid element including an active solid medium, and it is preferable that the laser rod 70 be alexandrite. The excitation lamp 71 is a light source that supplies energy for allowing the laser rod 70 to induce and emit light. For example, a rod-like flash lamp, which is filled with Xe gas, can be employed as the excitation lamp 71. The laser chamber 72 includes the laser rod 70 and the excitation lamp 71, and is a member for condensing light, which is emitted from the excitation lamp 71, on the laser rod 70. The laser chamber 72 is formed so that a coolant flowing in from a pipe 79a passes through the laser chamber 72 and flows out of a pipe 79b. The Q-switch 32 is disposed between the laser rod 70 and the total reflection mirror 74 on an optical axis of a beam Lo that is induced and emitted. The Q-switch 32 includes, for example, a $\lambda/4$ plate 75, a Pockels cell 76, and a polarizer 77. The housing 78 includes an opening 78a which is formed at the side wall of a portion thereof facing the output mirror 73 and through which the laser beam Lo is emitted. Meanwhile, the oscillator 30 may include other optical elements as necessary.

For example, the oscillator 30 is a Q-switch alexandrite laser in this embodiment. It is preferable that the oscillator 30 output pulse light having a pulse width of 1 to 150 nsec as a laser beam L. In this case, the pulse width of the laser beam L is controlled by, for example, the Q-switch. The wavelength of the laser beam is appropriately determined depending on the optical absorption property of a material present in a subject that is an object to be measured. For example, when an object to be measured is hemoglobin present in a living body (that is, when a blood vessel is imaged), it is preferable that the wavelength of a laser beam generally be a wavelength belonging to a near-infrared wavelength region. The near-infrared wavelength region means a wavelength region of about 700 to 850 nm. However, it is natural that the wavelength of a laser beam is not limited thereto. Further, laser beams L may have a short wavelength, and may have a plurality of wavelengths (for example, 750 nm and 800 nm). Furthermore, when the laser beams L have a plurality of wavelengths, the subject M may be simultaneously irradiated with the beams having these wavelengths and may be irradiated with the beams while the beams are alternately switched. The oscillator 30 may be a YAG-SHG-OPO laser or a Ti-Sapphire laser, which can output a laser beam corresponding to a near-infrared wavelength region likewise, other than the alexandrite laser.

The diffusion part 80 increases the diameter of the laser beam L by diffusing the laser beam L that is output from the oscillator 30. That is, the diffusion part 80 functions to increase the distribution of a propagation angle of light flux, which is included in the laser beam L, by allowing the laser beam L to pass through the diffusion part once. Accordingly, since the light-emitting surface of the diffusion part 80 serves as a secondary light source of the laser beam L, it is possible to prevent the laser beam L from being excessively narrowed when the laser beam L is condensed by the condensing lens system 81. The diffusion part 80 is disposed at a position where the laser beam L output from the oscillator 30 is received. Meanwhile, other optical elements can be provided between the oscillator 30 and the diffusion part 80 as necessary.

It is preferable that the diffusion part 80 be a diffuser, and it is particularly preferable that the diffusion part 80 be a lens diffuser. Further, a diffusion angle of the diffusion part 80 is preferably in the range of 0.2 to 5.0° and more preferably in the range of 0.4 to 3.0°. The reason for this is that diffusion efficiency is high. For example, a holographic diffuser, which is a lens diffuser in which small convex lenses are randomly disposed on the surface (for example, one surface) of a substrate, can be employed as the diffusion part 80. For example, a holographic diffuser manufactured by Edmunds (Model No.: 48513-L, material: quartz, diffusion angle: 0.5°, and transmission efficiency: 93%) can be used as this holographic diffuser.

Furthermore, it is preferable that the diffusion part 80 be a homogenizer. The homogenizer is an optical element that makes the top of the energy profile (energy distribution) of the laser beam L, which is incident from the upstream side of the optical system, flat and diffuses the laser beam L. The laser beam L of which the top has been made flat is guided to the condensing lens system 81, and is incident on the light incident-side end portion 82e of the optical fiber cable 82 while having a flat-top energy profile. In other words, "making the top of the energy profile flat" is to form a laser beam, which is incident on the homogenizer, into a laser beam of which the central portion has a flat-top energy profile. In this specification, "flat-top" means a state in which, when a concentric circle in which the diameter of the energy profile of the laser beam emitted from the homogenizer is 80% of the beam diameter is taken and a standard deviation of the energy of each point in this concentric circle is within 25% of average energy in this concentric circle. In general, the structure of the homogenizer is designed so that light is made completely flat-top at infinity (that is, the standard deviation is substantially equal to 0). However, in the invention, an energy profile, when a laser beam is incident on the light incident-side end portion 82e of the optical fiber cable 82, does not necessarily need to be in a completely flat-top state, and is sufficient to be in a flat-top state substantially corresponding to the above-mentioned range. Since a local increase in the intensity of light is further prevented when the top of the energy profile of the laser beam L is made flat, damage to the optical fiber cable 82 is also further suppressed.

The homogenizer may be formed of a single optical element, and may be formed of a combination of a plurality of optical elements. When the homogenizer is formed of a single optical element, it is preferable that a lens diffuser in which small concave lenses or the like are randomly disposed on the surface (for example, one surface) of a substrate be used as the homogenizer. For example, an engineered diffuser manufactured by RPC Photonics, Inc. (Model No.: EDC-2.0-A and diffusion angle: 2.0°) can be used as this lens diffuser. It is possible to substantially arbitrarily change the energy profile and the shape of the laser beam L by using these elements. When the homogenizer is formed of a single optical element as described above, the configuration of the diffusion part can be simplified.

Figure 4A:
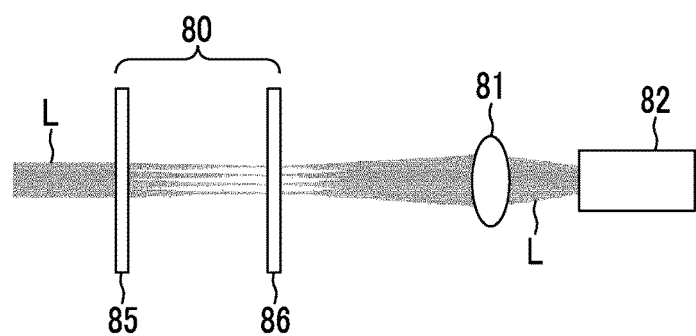
FIGS. 4A and 4B are schematic views showing examples of the configuration of an optical system that includes a diffusion part, a condensing lens system, and an optical fiber cable.
Figure 4B:
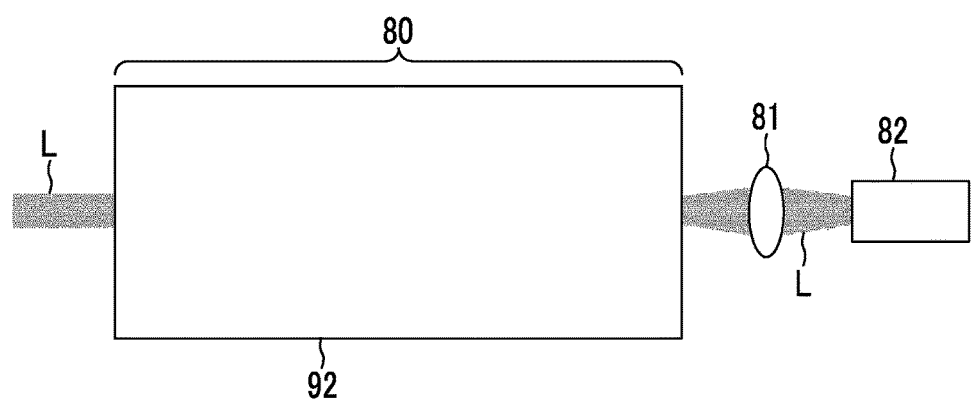

Meanwhile, even when the homogenizer is formed of a plurality of optical elements, an effect of adjusting a beam diameter, which is obtained after the condensation of light, to a predetermined value by the control of the distribution of an angle of a beam as in the diffuser only has to be obtained and, for example, the following configuration can be used. FIGS. 4A and 4B are schematic views showing examples of the configuration of an optical system of the diffusion part 80. The homogenizer as the diffusion part 80 may have a configuration in which, for example, a microlens array 85 and a microlens array 86 are disposed as shown in FIG. 4A. Further, the homogenizer can be formed of a flat-top laser beam shaper 92 in which, for example, an aspherical lens for correcting the energy profile of a beam or the distribution of an angle of a beam is assembled as shown in FIG. 4B.

The condensing lens system 81 guides the laser beam L, which has passed through the diffusion part 80, to the light incident-side end portion 82e of the optical fiber cable 82. The focal length of the condensing lens system 81 (a distance between a focal point and a main point on the optical fiber cable 82) is preferably in the range of 10 to 100 mm and more preferably in the range of 15 to 50 mm. The reason for this is that the size of the optical system can be reduced and a focal length is matched to the numerical aperture NA (about 0.22 at a maximum) of a general optical fiber of which a core is made of quartz and a clad is made of fluorine-doped quartz. Further, the condensing lens system 81 may be a coupled lens that includes a plurality of lenses. When the condensing lens system 81 is a coupled lens, the focal length of the condensing lens system 81 means the composite focal length of the coupled lens.

A distance between the diffusion part 80 and the condensing lens system 81 is appropriately adjusted so that the laser beam L diffused by the diffusion part 80 is efficiently coupled to the condensing lens system 81. In this case, it is preferable that the diffusion part 80 be disposed on the upstream side of the condensing lens system 81 in the optical system and within a range corresponding to three times a focal length from the center of the condensing lens system 81.

The optical fiber cable 82 transmits the laser beam L, which has been condensed by the condensing lens system 81, to the receptacle 51b to be described below. The optical fiber cable 82 corresponds to a light transmitting part of the invention. Meanwhile, the light transmitting part of the invention does not need to be an optical fiber cable that includes an optical fiber and a covering member for covering the optical fiber, and may be formed of only an optical fiber. The optical fiber cable 82 may be fixed to the receptacle 51b, and may be detachably fixed to the receptacle 51b. As long as the optical fiber cable 82 can be fixed to the receptacle 51b at least when a laser beam L is emitted from the optical fiber cable 82, an object of the invention can be achieved. The optical fiber cable 82 includes, for example, an optical fiber that includes a core and a clad, and covering members such as a ferrule and a sheath covering the periphery of the optical fiber. The optical fiber cable 82 may be a single fiber and may be a bundle fiber. However, since a coupling loss is large when the optical fiber cable 82 is a bundle fiber, it is preferable that the optical fiber cable 82 be a single fiber. When the optical fiber cable 82 is a single fiber, the diameter of a core of an optical fiber of the optical fiber cable is preferably in the range of 100 to 2000 μm and more preferably in the range of 200 to 1200 μm. The optical fiber of the optical fiber cable 82 is not particularly limited, but it is preferable that the optical fiber of the optical fiber cable 82 be a quartz fiber. An SMA-type optical fiber manufactured by Thorlabs Inc. can be used as the optical fiber cable 82.

Further, it is preferable that the optical fiber cable 82 include a light energy resistant structure at a light incident-side end portion thereof. In this specification, the "light energy resistant structure" means a structure that suppresses damage caused by the energy of a laser beam. Specifically, a so-called air gap-optical fiber cable including an air gap 88 can be used as the optical fiber cable 82 including the light energy resistant structure. For example, an optical fiber cable 82 (FIG. 5) that includes an optical fiber 82a of which the damage threshold energy density of a clad 84b (the intensity of energy per unit area when the structure of the clad 84b starts to be damaged by the energy of a laser beam) is substantially equal to the damage threshold energy density of a core 84a (for example, an optical fiber of which a core is made of quartz and a clad is made of fluorine-doped quartz, or the like) and a ferrule 87a that covers the optical fiber 82a so that the side surface of the clad 84b near an end face of the clad 84b is exposed to the outside; an optical fiber cable that includes an optical fiber of which a clad near an end face is removed and the side surface of a core near the end face is exposed to the outside, and a ferrule that covers the optical fiber so that the side surface of the core near the end face is exposed to the outside; and an optical fiber cable 82 (FIG. 6) that includes an optical fiber 82a having a structure (end cap structure) in which a member 88a made of a material (quartz or the like) of which the damage threshold energy density is substantially equal to the damage threshold energy density of a core 84a is connected to an end portion and a ferrule 87a that covers the optical fiber 82a so that the side surface of the member 88a is exposed to the outside can be used as the air gap-optical fiber cable.

When the optical fiber cable 82 is an air gap-optical fiber cable having a structure in which the side surface of the core 84a or the clad 84b near the end face thereof is exposed to the outside, it is preferable that an exposed range of the core 84a or the clad 84b be set in the range of 1 to 3 mm from the end of the optical fiber cable. The reason why the exposed range of the core 84a or the clad 84b is set to 1 mm or more is that a distance between a material provided around the core 84a or the clad 84b and the end of the optical fiber cable 82 needs to be set so that the energy density of light emitted to the outside of the core is reduced and energy absorbed by the material provided around the core 84a or the clad 84b becomes smaller than the damage threshold energy of the material. Further, the reason why the exposed range of the core 84a or the clad 84b is set to 3 mm or less is to prevent the occurrence of damage to the optical fiber cable that is caused by bending and folding when a light incident surface of the end face of the optical fiber cable 82 is polished. The optical fiber 82a of the optical fiber cable 82 is not particularly limited, but it is preferable that the optical fiber 82a be a quartz fiber. It is possible to produce the air gap-optical fiber cable by, for example, polishing the end faces of a quartz fiber and a commercially available air gap-ferrule after inserting the quartz fiber into the commercially available air gap-ferrule and fixing the quartz fiber by adhesion.

Furthermore, an optical fiber cable 82 (FIG. 7), which includes an optical fiber 82a and a ferrule 87b, can also be used as the optical fiber cable 82 including the light energy resistant structure. The optical fiber 82a includes a core 84a and a clad 84b. The ferrule 87b covers the optical fiber, and is made of a material (quartz, zirconia, sapphire, or the like) of which the damage threshold energy density is equal to or higher than the damage threshold energy density of the core 84a. The side surface of the optical fiber 82a and the inner peripheral surface of the ferrule 87b are fixed to each other by an adhesive at portions of the optical fiber cable except for the vicinity of the end face of the optical fiber cable. In the optical fiber cable 82 shown in FIG. 7, it is preferable that "the vicinity of the end faces" be in the range of 1 to 3 mm in terms of damage to an adhesive caused by light energy and the strength of fixing and adhesion.

Figure 5:
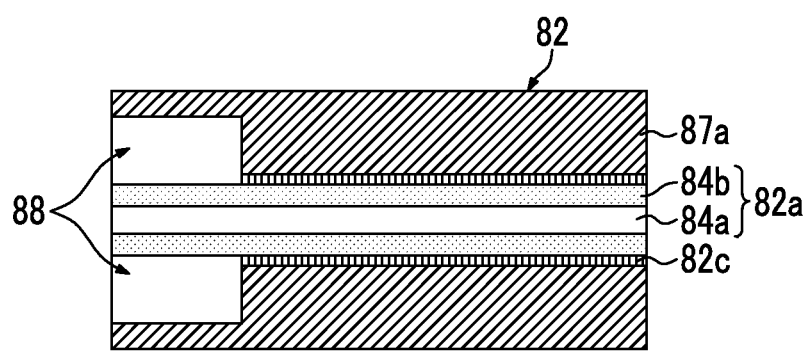
FIG. 5 is a schematic cross-sectional view showing an embodiment of an optical fiber that includes a light energy resistant structure at an end portion thereof.
Figure 6:
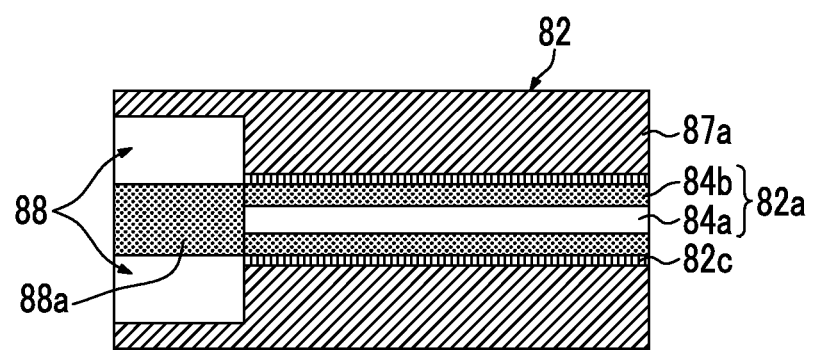
FIG. 6 is a schematic cross-sectional view showing another embodiment of the optical fiber that includes the light energy resistant structure at the end portion thereof.
Figure 7:
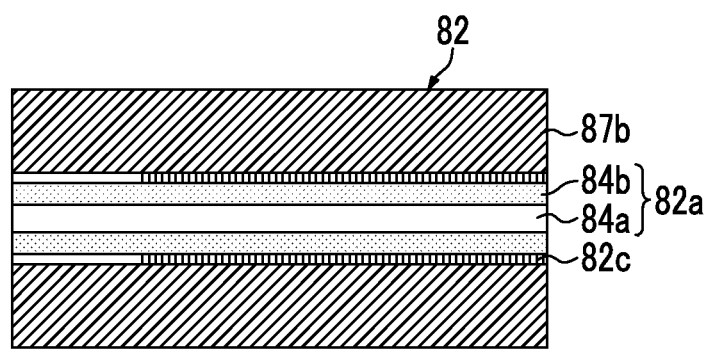
FIG. 7 is a schematic cross-sectional view showing another embodiment of the optical fiber that includes the light energy resistant structure at the end portion thereof.

Meanwhile, in the optical fiber cables 82 shown in FIGS. 5 to 7, the optical fiber 82a and the ferrule 87a or 87b are fixed to each other by an adhesive 82c.

The position of the optical fiber cable 82 is adjusted so that, for example, an incident end of the optical fiber of the optical fiber cable 82 is positioned at the focal point of the condensing lens system 81. An optical fiber cable-position adjusting unit, which moves the optical fiber cable 82 in the direction of the optical axis of the optical fiber cable 82, may be provided so that the position of the optical fiber cable 82 can be finely adjusted. Accordingly, it is possible to adjust the position of the optical fiber cable in the vicinity of the position of a focal point without the deterioration of a flat-top property, and it is also possible to finely adjust a beam diameter when the beam is incident on the light incident-side end portion 82e.

If the diameter of the core of the optical fiber 82a of the light transmitting part (optical fiber cable 82) is reduced to a diameter substantially equal to or smaller than the diameter of the optical fiber 40 of the probe 11 and the light-emitting end face of the optical fiber 82a and the light incident end face of the optical fiber 40 are disposed close to each other, light does not spread around the optical fiber and a loss in the connection between these optical fibers 82a and 40 can be suppressed. Accordingly, an effect of improving the transmission efficiency of energy is obtained even on the light-emitting side of a single fiber.

In particular, when the optical fiber 40 (light guide part) of the probe 11 is a bundle fiber, it is preferable that the diameter $d_{out}$ of the core of the optical fiber 82a of the light transmitting part on the light-emitting side and a bundle diameter B of the bundle fiber satisfy the following expression 3. The bundle diameter means the maximum distance between optical fibers, which are most distant from each other, among a plurality of optical fibers of the bundle fiber on the circumference of the core.

$$0.8\ B \leq d_{out} \leq 1.2B \qquad \text{Expression 3}$$

The reason for this is as follows. In the invention, there is also an advantage (second effect) of making the top of the energy profile of a laser beam flat since a laser beam is repeatedly reflected in the optical fiber 82a. This causes an effect of further ensuring the uniformity of light distribution at the end of the probe since substantially the same energy can be input to the respective fiber wires included in a bundle fiber, particularly, when the optical fiber 40 of the probe 11 is the bundle fiber. According to experiments performed by the inventor, when a laser beam of which the top was made flat by an engineered diffuser (homogenizer) and a condensing lens was directly incident on a bundle fiber without passing through an optical fiber, the energy transmission efficiency of the entire system between a light source and an emission-side end portion of the bundle fiber was about 50% at the most. Meanwhile, when a laser beam was incident on a bundle fiber after the laser beam passing through a holographic diffuser and a condensing lens was transmitted through a single fiber so that the top of the laser beam was made flat, the transmission efficiency was surprisingly increased up to about 61% even though a homogenizer was not used. In particular, when "$0.8B \leq d_{out} \leq 1.2B$" is satisfied in a relationship between the diameter $d_{out}$ of the core of the single fiber and the bundle diameter B of the bundle fiber, superiority to transmission efficiency, which is obtained when the optical fiber 40 of the probe 11 is a single fiber, and the uniformity of the light distribution are compatible with each other.

The connector 51 is a connecting member that optically connects the optical fiber 40 to an optical system provided in the unit housing 13b. For example, a known optical connector can be used as this connector. The connector 51 includes a plug 51a and a receptacle 51b that has a structure corresponding to the plug 51a and is detachably connected to the plug 51a. The plug 51a and the receptacle 51b correspond to a connector portion and a connector receiving portion of the invention, respectively. Meanwhile, the receptacle 51b itself may include an optical member that connects an emission-side end face of the optical fiber cable 82 to a light incident-side end face of the optical fiber 40.

<PC>

A PC 17 includes a user interface as input means 16 and a monitor as image display means 14, and is connected to the ultrasonic unit 12 by a cable 17a. A user can input conditions of photoacoustic measurement or check a photoacoustic image by using the PC 17. Meanwhile, the PC may be integrated with the ultrasonic unit.

Next, the detail configuration of the ultrasonic unit and a process for forming a photoacoustic image will be described.

As shown in FIG. 2, the ultrasonic unit 12 includes a receiving circuit 21, AD conversion means 22, a receiving memory 23, photoacoustic image reconstruction means 24, detection/logarithmic conversion means 27, photoacoustic image construction means 28, control means 60, image synthesizing means 38, and observing method selection means 39.

The control means 60 controls each part of the photoacoustic image forming apparatus 10, and includes a trigger control circuit 66 in this embodiment. The trigger control circuit 66 transmits an optical trigger signal to the control means 61 of the laser unit 13 as a control signal, for example, at the time of the start of the photoacoustic image forming apparatus. Accordingly, in the laser unit 13, a flash lamp 31 is turned on, the excitation of the laser rod is started, and preparation for the output of laser is started. Then, the excitation state of the laser rod is maintained and the laser unit 13 can output a pulse laser beam.

After that, the control means 60 transmits a Q-switch trigger signal to the control means 61 of the laser unit 13 from the trigger control circuit 66 as a control signal. The control means 61, which has received the Q-switch trigger signal, controls the Q-switch 32 to allow a laser beam L to be output. That is, the control means 60 controls the output timing of a pulse laser beam, which is to be output from the laser unit 13, by the Q-switch trigger signal. Further, in this embodiment, the control means 60 transmits the Q-switch trigger signal and transmits a sampling trigger signal to the AD conversion means 22 at the same time. The sampling trigger signal serves as a signal for the start timing of the sampling of photoacoustic signals of the AD conversion means 22. It is possible to sample the photoacoustic signals in synchronization with the output of a laser beam by using the sampling trigger signal as described above.

The receiving circuit 21 receives photoacoustic signals that are generated by the probe 11. The photoacoustic signals, which are received by the receiving circuit 21, are transmitted to the AD conversion means 22.

The AD conversion means 22 is sampling means, and samples photoacoustic signals, which are received by the receiving circuit 21, and converts the sampled photoacoustic signal into a digital signal. For example, the AD conversion means 22 includes a sampling controller and an AD converter. Received signals, which are received by the receiving circuit 21, are converted into sampling signals that are digitized by the AD converter. The AD converter is controlled by the sampling controller, and is adapted to start sampling when the sampling controller receives a sampling trigger signal. The AD conversion means 22 samples the received signals at a predetermined sampling cycle on the basis of, for example, AD clock signals that are input from the outside and have a predetermined frequency.

The receiving memory 23 stores a photoacoustic signal that is sampled by the AD conversion means 22 (that is, the sampling signal). Further, the receiving memory 23 outputs the photoacoustic signal to the photoacoustic image reconstruction means 24.

The photoacoustic image reconstruction means 24 reads out photoacoustic signals from the receiving memory 23, and generates data of the respective lines of a photoacoustic image on the basis of the photoacoustic signals that are detected by the acoustic detector 42 of the probe 11. The photoacoustic image reconstruction means 24 generates data corresponding to one line by adding, for example, data, which is obtained from sixty-four acoustic detecting elements of the probe 11, at a delay time corresponding to the positions of the acoustic detecting elements (delay addition method). The photoacoustic image reconstruction means 24 may perform reconstruction by a CBP method (Circular Back Projection) instead of the delay addition method. Alternatively, the photoacoustic image reconstruction means 24 may perform reconstruction by a Hough transform method or a Fourier transform method.

The detection/logarithmic conversion means 27 obtains an envelope of data of each line, and logarithmically converts the envelope.

The photoacoustic image construction means 28 constructs a photoacoustic image, which corresponds to one frame, on the basis of the data of each line that has been subjected to logarithmic conversion. The photoacoustic image construction means 28 constructs a photoacoustic image by converting the position of a photoacoustic signal (peak portion) in the direction of a time axis into a position in a depth direction of the photoacoustic image.

The observing method selection means 39 selects the display mode of the photoacoustic image. Examples of the display mode of volume data of the photoacoustic signals include a mode of a three-dimensional image, a mode of a sectional image, and a mode of a graph on a predetermined axis. A display mode is selected according to a default or an input that is input from the input means 16 by a user.

The image synthesizing means 38 generates volume data by using photoacoustic signals that are sequentially acquired. The generation of volume data is performed by assigning the values of the respective photoacoustic signals to virtual spaces according to coordinates associated with the frames of the photoacoustic image and coordinates of pixels of the photoacoustic image. If places to which the signal values are assigned overlap each other when the values of the signals are assigned, for example, an average value of the signal values of the overlapping places or the maximum value among the signal values is employed as the signal value of the overlapping place. Further, when there is no signal value to be assigned, it is preferable that a signal value be interpolated by using the values of peripheral signals. Furthermore, the image synthesizing means 38 performs necessary processing (for example, the correction of a scale, coloring corresponding to a voxel value, and the like) on the generated volume data.

Moreover, the image synthesizing means 38 forms a photoacoustic image according to an observing method that is selected by the observing method selection means 39. The photoacoustic image, which is formed according to the selected observing method, is the final image (display image) to be displayed on the image display means 14.

The image display means 14 displays the display image that is formed by the image synthesizing means 38.

<Effect>

The effect of the photoacoustic image forming apparatus of this embodiment will be described below.

When the transmission of a laser beam in the unit housing 13*b* is space transmission as described above, the incident position of a laser beam incident on the connector receiving portion (receptacle 51*b*) is shifted and the amount of energy to be transmitted is not stable. For this reason, there is a problem in that transmission efficiency is lowered. Here, in the invention, the transmission of a laser beam to the receptacle 51*b* is performed by using the optical fiber cable 82 (optical fiber) for the prevention of the shift of the incident position of a laser beam L. At this time, one end of the optical fiber cable 82 is fixed to the optical system provided in the housing and the other end thereof is fixed to the receptacle 51*b*. Accordingly, even though the oscillator 30 provided in the unit housing 13*b* and a housing wall move in different manners with a temperature change and the like, the incident position of a laser beam L incident on the receptacle 51*b* is not shifted.

However, it is not possible to avoid a problem, such as the breakage of the optical fiber cable 82, in photoacoustic measurement requiring large light energy (1 mJ or more) by only optical fiber transmission.

Further, in the invention, a laser beam L passes through the diffusion part 80 once, so that the distribution of a propagation angle of light flux, which is included in the laser beam L, is increased. Furthermore, a beam diameter, which is obtained when the beam is incident on the optical fiber cable 82, is controlled by using the focal length of the condensing lens system 81, so that the excessive narrowing of the laser beam is prevented when the laser beam condensed by the condensing lens system 81 is incident on the optical fiber.

Moreover, in this embodiment, when the optical fiber cable 82 includes the light energy resistant structure at the light incident-side end portion thereof, the condensing lens system 81 condenses a laser beam so that the minimum beam diameter D of the laser beam L defined by the following expression 4 (that is, the diameter of a beam condensed on a focal plane) is $d_{in}/2$ or more in a relationship between the diameter $d_{in}$ of the core of the optical fiber cable 82 on the light incident side and the minimum beam diameter D. It is preferable that a light incident-side end face of the core of the optical fiber cable 82 be disposed so that a laser beam L is incident on the light incident-side end face of the core while the diameter of the laser beam is $d_{in}/2$ or more.

$$D = A \cdot f \cdot \tan\left(\sqrt{\left(\frac{\phi}{2}\right)^2 + \left(\frac{\theta}{2}\right)^2}\right) \quad \text{Expression 4}$$

In Expression 4, A denotes a coefficient that is determined depending on the kind of the diffusion part 80, f denotes the focal length of the condensing lens system 81, φ denotes the spread angle of a laser beam L when the laser beam is incident on the diffusion part 80, and θ denotes the diffusion angle of the diffusion part 80. Here, the "spread angle" means an angle where the diameter of a laser beam L is increased with the propagation of the laser beam. Further, the "diffusion angle" of the diffusion part 80 means a design diffusion angle, that is, an angle where the diameter of a laser beam L as parallel light incident on and transmitted through the diffusion part 80 is increased with the propagation of the laser beam. Meanwhile, the "spread angle" and the "diffusion angle" are represented by a total plane angle. When these angles are to be measured, it is preferable that a beam diameter be measured at about 10 points within a range of a propagation distance until a certain beam diameter is increased to double the beam diameter and the angles be obtained from the inclination of the change of the beam diameter at this time. Furthermore, the "beam diameter" is set to the diameter of a circle which includes about 86.5% energy and of which the center is positioned on a beam center (generally, a position where the intensity of a beam is the maximum) in the energy profile of the laser beam L, that is, a so-called $1/e^2$ diameter. In this case, when it is difficult to obtain a beam center due to the irregular distribution of the intensity of a beam, or the like, circles in which energy is 86.5% in the vicinity of a position that is estimated as the beam center are exhaustively made and the diameter of a circle having the minimum area among these circles may be used as the beam diameter.

The reason why the beam diameter D is set to ½ or more of the diameter $d_{in}$ of the core of the optical fiber 82*a* is to suppress damage to the core 84*a* of the optical fiber 82*a* (core damage mode) that is caused by the concentration of energy occurring due to the reduction of the beam diameter. Further, the reason for this is also that an advantage of the use of the optical fiber including the light energy resistant structure at the end portion thereof is large in a range in which the beam diameter is ½ or more of the diameter of the core of the optical fiber 82*a*.

Meanwhile, when the optical fiber cable 82 does not include the light energy resistant structure at the light incident-side end portion thereof, the condensing lens system 81 condenses a laser beam so that the minimum beam diameter D of the laser beam L is in the range of $d_{in}/3$ to $2d_{in}/3$ in a relationship between the diameter $d_{in}$ of the core of the optical fiber cable 82 on the light incident side and the minimum beam diameter D. It is preferable that a light incident-side end face of the core of the optical fiber cable 82 be disposed so that a laser beam L is incident on the light incident-side end face of the core while the diameter of the laser beam L is in the range of $d_{in}/3$ to $2d_{in}/3$.

The reason why the beam diameter D is set to ⅓ or more of the diameter $d_{in}$ of the core of the optical fiber 82*a* is to suppress the occurrence of the core damage mode that is caused by the concentration of energy occurring due to the reduction of the beam diameter.

Further, the reason why the beam diameter D is set to ⅔ or less of the diameter $d_{in}$ of the core of the optical fiber 82a is to suppress the absorption of the energy of the laser beam in members provided around the core of the optical fiber 82a and damage to the members caused by an increase in the beam diameter D, and is to suppress the discharge of emissions, such as dust and gas, from damaged portions. These emissions adhere to the end face of the optical fiber, cause the breakage of the core near the end face, and cause a problem (peripheral damage mode) in that the transmission of energy is inhibited. That is, the reason why the beam diameter is set to ⅔ or less of the diameter of the core of the optical fiber is to suppress the occurrence of the peripheral damage mode. The members provided around the core mean, for example, a clad that is made of a resin, an adhesive and a coating that cover the outer surface of the clad, and a covering member such as a ferrule that covers the outer periphery of the adhesive and the coating and is made of metal.

The control of the beam diameter D of the laser beam L and the above-mentioned numerical value ranges will be described in more detail below.

Figure 8:
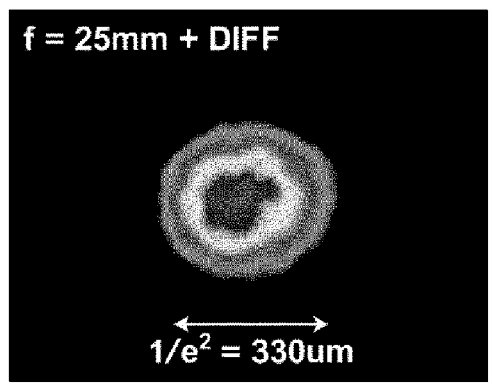
FIG. 8 is a view showing the energy profile of a beam at a lens focus position when a laser beam diffused by a diffuser is condensed by the condensing lens system.
Figure 9:
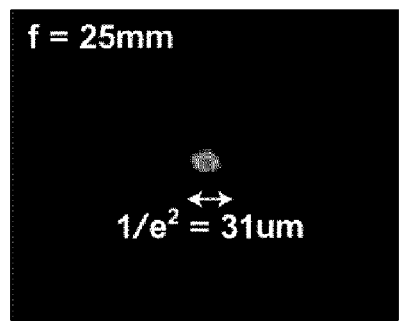
FIG. 9 is a view showing the energy profile of a beam at the lens focus position when the diffuser is not used and the laser beam is condensed by the condensing lens system.

FIG. 8 is a view showing the energy profile of a beam at a lens focus position when a laser beam diffused by the diffuser is condensed by the condensing lens system, and FIG. 9 is a view showing the energy profile of a beam at the lens focus position when the diffuser is not used and the laser beam is condensed by the condensing lens system. The focal length of the condensing lens system 81 is 25 mm in all the cases of FIGS. 8 and 9, but it is understood that the minimum beam diameter in the case using the diffuser is 330 μm and is larger than the minimum beam diameter (31 μm) in the case not using the diffuser. In general, since the spread angle φ of a laser beam, when the laser beam is output from the oscillator, is small (about 0.15° at the most), a condensed laser beam is narrowed at the incident end of the optical fiber cable 82. As a result, since the energy of the laser beam is concentrated on the incident end of the optical fiber cable 82, damage to the core on the end face of the optical fiber cable 82 occurs. Further, FIG. 10A is a view showing the energy profile of a laser beam L, which is condensed by a lens after the top of the energy profile of the laser beam is made flat by the homogenizer, on a focal plane. Furthermore, FIG. 10B is a view showing the energy profile of a laser beam, which is condensed by a lens after the laser beam is diffused by a holographic diffuser without the use of the homogenizer, on a focal plane. From FIGS. 10A and 10B, it is understood that a ratio of FWHM (full width at half maximum) W1 to the minimum beam diameter D1 of a laser beam in FIG. 10A is larger than a ratio of FWEIM W2 to the minimum beam diameter D2 of a laser beam in FIG. 10B. When a laser beam has this flat-top profile, the local concentration of energy is further suppressed. Accordingly, even though a beam having higher energy is incident on an optical fiber, it is possible to prevent damage to the optical fiber.

Figure 11:
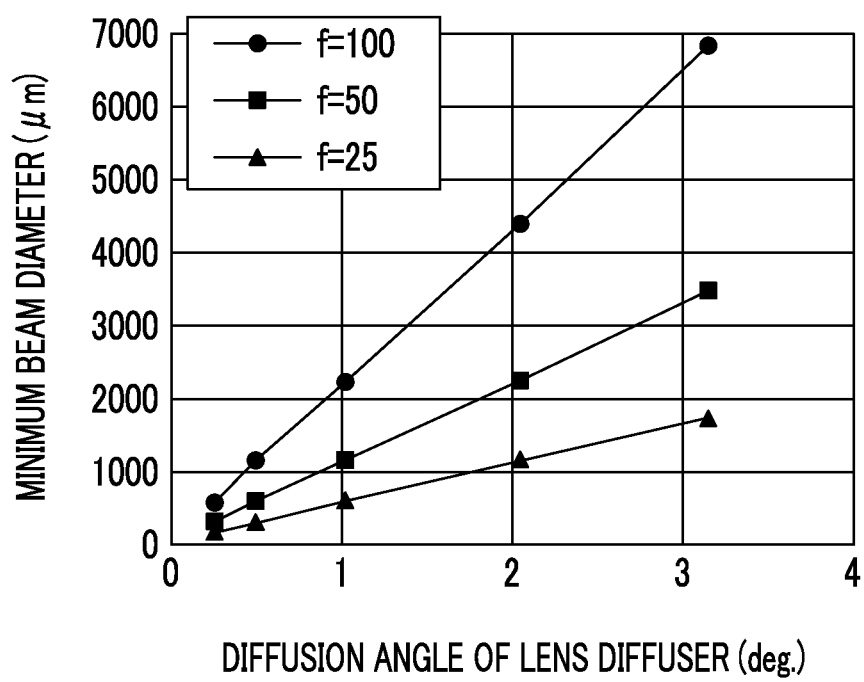
FIG. 11 is a graph showing a relationship between the optical characteristics of a lens diffuser and the condensing lens system and the minimum beam diameter.

Further, the laser beam L is diffused by the diffusion part 80 in the invention, so that the diameter of the laser beam L is controlled at the lens focus position. FIG. 11 is a graph showing, for example, a relationship between the optical characteristics of the lens diffuser (engineered diffuser) and the condensing lens system and the minimum beam diameter. In this graph, a horizontal axis represents the diffusion angle (deg.) of the lens diffuser and a vertical axis represents the minimum beam diameter (μm). Furthermore, a round plot of the graph shows data when the focal length of the condensing lens system is 100 mm, a square plot shows data when the focal length of the condensing lens system is 50 mm, and a triangular plot shows data when the focal length of the condensing lens system is 25 mm. From FIG. 11, it is understood that the minimum beam diameter can be adjusted through the adjustment of the optical characteristics of the diffuser and the condensing lens system. Meanwhile, even in regard to a diffuser (for example, a holographic diffuser), such as an engineered diffuser, other than a homogenizer, the tendency of the change of the minimum beam diameter relative to the diffusion angle of a lens diffuser is the same as described above.

When parallel light, which travels in a direction forming an angle α between the optical axis of the condensing lens system and the parallel light, is incident on the condensing lens system having a focal length f, the position of a light-condensing point where the parallel light is condensed is shifted from the position of the focal point of the condensing lens system and a distance between the light-condensing point and the focal point can be approximated by f·tan α. The invention is an invention in which this principle is used in a method of controlling a beam diameter.

Accordingly, when an angle between the travelling direction of laser beam flux, which is incident on the condensing lens system, and the optical axis of the condensing lens system has a distribution, laser beam flux is condensed at positions corresponding to the respective angles. Therefore, the light condensing range of all laser beams in which light-condensing points corresponding to the respective angles are superimposed becomes large. For example, when the diffuser is disposed on the upstream side of the condensing lens system, the angle distribution of the laser beam flux, which has been within about φ/2 before the laser beam flux is incident on the diffuser, is increased with a half angle within $\sqrt{((\varphi/2)^2+(\theta/2)^2)}$ after the laser beam flux is transmitted through the diffuser. Accordingly, the light condensing range of all laser beams, which are condensed subsequently by the condensing lens system so as to correspond to this angle distribution, becomes large in comparison with a case in which the laser beam flux is not transmitted through the diffuser.

Further, considering that the $1/e^2$ diameter of a laser beam is used as the beam diameter in the light condensing range, it is estimated that a diameter $2f \cdot \tan(\sqrt{((\varphi/2)^2+(\theta/2)^2)})$ of the light condensing range and the minimum beam diameter D have a constant correlationship therebetween.

Figure 12:
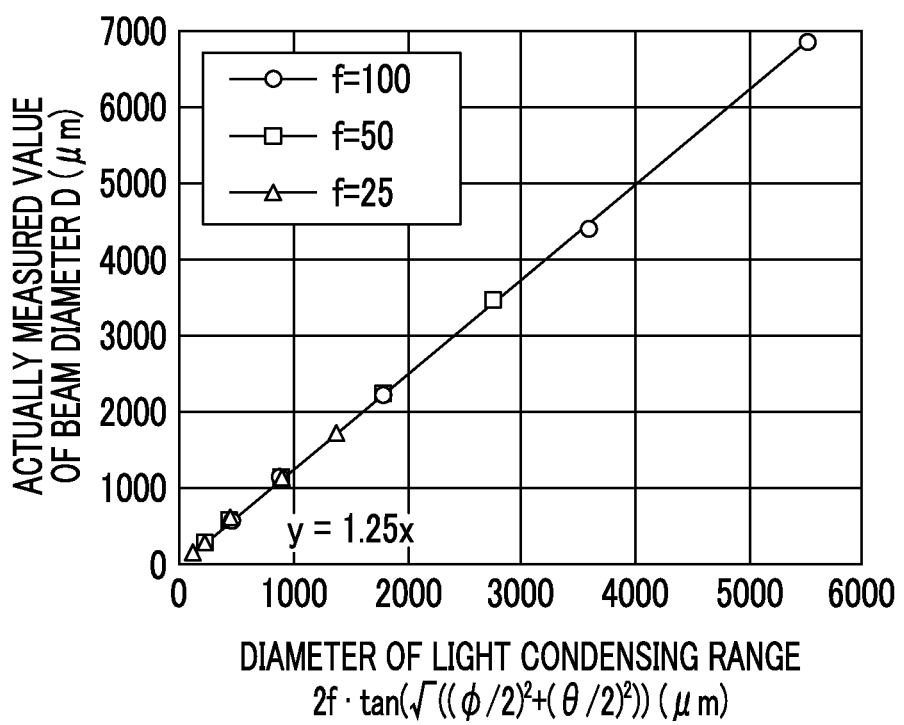
FIG. 12 is a graph showing a correlationship between the diameter of a light condensing range and the minimum beam diameter when laser beam flux in which an angle between a travelling direction and an optical axis of the condensing lens system has a distribution is condensed by the condensing lens system (when the engineered diffuser is used).

FIG. 12 is a graph showing a correlationship between the diameter $2f \cdot \tan(\sqrt{((\varphi/2)^2+(\theta/2)^2)})$ of a light condensing range and an actual minimum beam diameter D, which is experimentally obtained, when laser beam flux in which an angle between a travelling direction and the optical axis of the condensing lens has a distribution is condensed on the condensing lens. More specifically, this graph shows the results of experiments that measure a light condensing range by a beam profiler (LaserCam-HR manufactured by Coherent Inc.) when a laser beam having a wavelength of 532 nm, a pulse width of 3.5 ns, a diameter of 3.5 mm when the laser beam is incident on a diffuser, and a spread angle φ of 0.13° is condensed by a condensing lens having a predetermined focal length f after the laser beam is incident on an engineered diffuser having a predetermined diffusion angle θ. Meanwhile, even when the diffusion angle of the diffuser is obtained, measurement is performed using the same beam profiler. Five round plots of the graph show results that are measured by an optical system using a combination of a condensing lens, which has a focal length f of 100 mm, and a diffuser, and the diffusion angle θ of the diffuser is 0.25°, 0.50°, 1.02°, 2.05°, and 3.15° from a plot that is positioned on the lower left side, respectively. Further, five square plots of the graph show results that are measured by an optical system using a combination of a condensing lens, which has a focal length f of 50 mm, and a diffuser, and the diffusion angle θ of the diffuser is 0.25°, 0.50°, 1.02°, 2.05°, and 3.15° from a plot that is positioned on the lower left side, respectively. Furthermore, five triangular plots of the graph show results that are measured by an optical system using a combination of a condensing lens, which has a focal length f of 25 mm, and a diffuser, and the diffusion angle θ of the diffuser is 0.25°, 0.50°, 1.02°, 2.05°, and 3.15° from a plot that is positioned on the lower left side, respectively.

From FIG. 12, it is understood that a relationship between the minimum beam diameter D and the diameter of the light condensing range corresponds to a linear function. Moreover, the inclination of the linear function of the graph is about 1.25. Accordingly, 2.5 is given as the coefficient A of Expression 4 in regard to, for example, an engineered diffuser.

Figure 13:
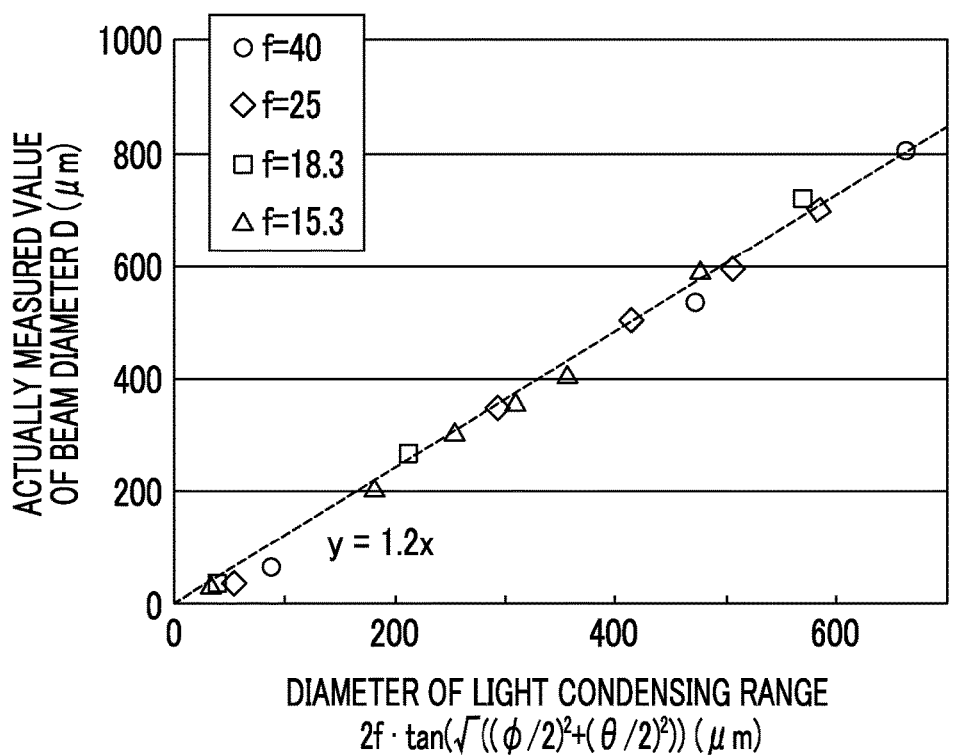
FIG. 13 is a graph showing a correlationship between the diameter of a light condensing range and the minimum beam diameter when laser beam flux in which an angle between a travelling direction and an optical axis of the condensing lens system has a distribution is condensed on the condensing lens system (when the holographic diffuser is used).

Further, likewise, FIG. 13 is a graph showing a correlationship between the diameter $2f \cdot \tan(\sqrt{((\varphi/2)^2+(\theta/2)^2)})$ of a light condensing range and an actual minimum beam diameter D that is experimentally obtained, and is a graph that is obtained using a holographic diffuser. More specifically, this graph shows the results of experiments that measure a light condensing range by a beam profiler when a laser beam having a wavelength of 532 nm, a pulse width of 3.5 ns, a diameter of 3.5 mm when the laser beam is incident on a diffuser, and a spread angle φ of 0.13° is condensed by a condensing lens having a predetermined focal length f after the laser beam is incident on a holographic diffuser having a predetermined diffusion angle θ. Three round plots of the graph show results that are measured by an optical system using a combination of a condensing lens, which has a focal length f of 40 mm, and a diffuser, and the diffusion angle θ of the diffuser is 0° (that is, there is no diffuser), 0.65°, and 0.95° from a plot that is positioned on the lower left side, respectively. Furthermore, five rhombic plots of the graph show results that are measured by an optical system using a combination of a condensing lens, which has a focal length f of 25 mm, and a diffuser, and the diffusion angle θ of the diffuser is 0°, 0.65°, 1.15°, and 1.35° from a plot that is positioned on the lower left side, respectively. Moreover, three square plots of the graph show results that are measured by an optical system using a combination of a condensing lens, which has a focal length f of 18.3 mm, and a diffuser, and the diffusion angle θ of the diffuser is 0°, 0.65°, and 1.80° from a plot that is positioned on the lower left side, respectively. Further, six triangular plots of the graph show results that are measured by an optical system using a combination of a condensing lens, which has a focal length f of 15.3 mm, and a diffuser, and the diffusion angle θ of the diffuser is 0°, 0.65°, 0.95°, 1.15°, 1.35° and 1.80° from a plot that is positioned on the lower left side, respectively.

In FIG. 13, the inclination of a linear function of the graph is about 1.2. Accordingly, 2.4 is given as the coefficient A of Expression 4 in regard to, for example, a holographic diffuser.

That is, in regard to a predetermined laser beam, a focal length and a diffusion angle are not limited to the focal lengths and the diffusion angles used in the above-mentioned experiments, and it is said that it is possible to form an arbitrary beam diameter D by appropriately setting the focal length f and the diffusion angle θ. Accordingly, since the diameter D of the laser beam L is controlled by using the above-mentioned relationship, it is possible to transmit a laser beam L having high energy by using the optical fiber cable 82 so that the energy density does not exceed the damage threshold energy density of the core 84a of the optical fiber 82a of the optical fiber cable 82.

Figure 14:
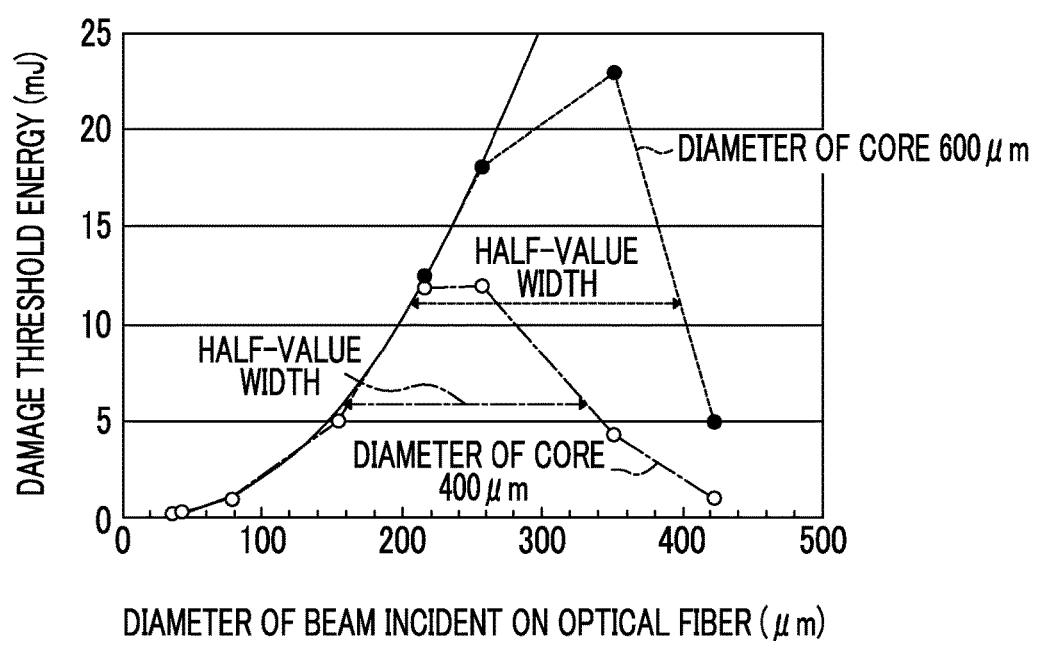
FIG. 14 is a graph showing a relationship between a beam diameter at the lens focus position and the damage threshold energy of a core of a general optical fiber cable, as a result in experiments in which conditions of the diffuser and the condensing lens system are changed.

For example, FIG. 14 is a graph showing a relationship between a beam diameter at a lens focus position and the damage threshold energy of an optical fiber cable, as a result in experiments in which conditions of a diffuser and a condensing lens are changed. More specifically, when a laser beam having a wavelength of 532 nm, a pulse width of 3.5 ns, a diameter of 3.5 mm when the laser beam is incident on a diffuser, and a spread angle φ of 0.13° is condensed on an end face of an optical fiber cable (having a core diameter of 600 μm or 400 μm) by a condensing lens having a predetermined focal length f after the laser beam is incident on a diffuser having a predetermined diffusion angle θ, a core damage mode or a peripheral damage mode occurs. The graph of FIG. 14 is a graph in which energy, which is obtained when the core damage mode or the peripheral damage mode starts to occur, is plotted. In experiments, the pulse laser beam is incident on one end portion of an optical fiber and the energy of a pulse laser beam emitted from the other end portion thereof is measured. Further, the maximum value of energy, which is measured on the emission side while the incident energy of the pulse laser beam is increased until a light incident-side end portion is damaged, is damage threshold energy. A beam diameter at the lens focus position is adjusted by the appropriate combination of a diffuser that has a diffusion angle θ of 0.65° or 1.8° and a condensing lens that has a focal length f of 11.0 mm, 15.3 mm, 18.3 mm, or 25.0 mm. In FIG. 14, a solid line represents a damage threshold energy curve of an end face of the optical fiber that is estimated from the damage threshold energy density of a quartz core. Furthermore, a dotted line represents the damage threshold energy of an optical fiber cable that includes a quartz core having a diameter of 600 μm. Moreover, a dashed-dotted line represents the damage threshold energy of an optical fiber cable that includes a quartz core having a diameter of 400 μm. The start point of a half-value width corresponds to about ⅓ of a core diameter d and the end point thereof corresponds to about ⅔ of the core diameter d.

From this graph, it is understood that the damage mode of the optical fiber is switched to the peripheral damage mode from the core damage mode during the increase of the beam diameter and damage threshold energy shows a change that is convex upward relative to a beam diameter. The reason for this is that the durability of the above-mentioned members, which are provided around the core, against a laser beam is lower than that of the core made of quartz or the like. That is, when the optical fiber cable 82 does not include the light energy resistant structure at the light incident-side end portion thereof, it is preferable that the light incident-side end face of the core of the optical fiber cable 82 be disposed so that a laser beam L is incident on the light incident-side end face of the core while the diameter of the laser beam L is in the range of $d_{in}/3$ to $2d_{in}/3$.

Further, since the control range of a beam diameter is limited to about 90 μm at the most in a method in the related art that condenses a laser beam on an optical fiber cable (having a core diameter of 600 μm) without the diffusion part 80, the limit of the amount of energy, which can be transmitted, is about 1.0 mJ as understood from the graph of FIG. 14. However, in the invention that controls the beam diameter D by the combination of the diffusion part 80 and the condensing lens system 81, a larger amount of energy can be transmitted as the beam diameter D is controlled to be increased. That is, according to FIG. 14, for example, an amount of energy of about 12 mJ can be transmitted when the diameter of the core of the optical fiber is 400 µm and a beam diameter is 250 µm, and an amount of energy of about 22 mJ, which is significantly large, can be transmitted when the diameter of the core of the optical fiber is 600 µm and a beam diameter is 350 µm. According to the invention, it is possible to significantly increase the amount of energy, which can be transmitted, as described above.

Figure 15:
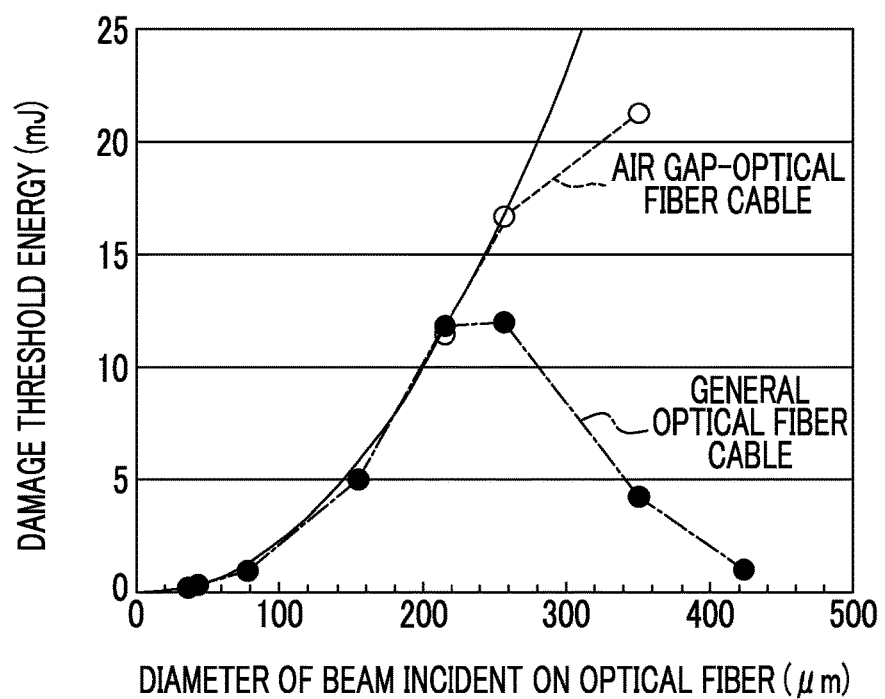
FIG. 15 is a graph showing a relationship between a beam diameter at the lens focus position and the damage threshold energy of a core of an air gap-optical fiber cable, as a result in experiments in which conditions of the diffuser and the condensing lens system are changed.

Furthermore, FIG. 15 is also a graph showing a relationship between a beam diameter at a lens focus position and the damage threshold energy of an optical fiber cable, as a result in experiments in which conditions of a diffuser and a condensing lens are changed. However, the graph is, particularly, a graph comparing an optical fiber cable that includes a light energy resistant structure with an optical fiber cable that does not include the light energy resistant structure. More specifically, when a laser beam is condensed on an end face of an optical fiber cable 82 having an air gap or an end face of a general optical fiber cable by a condensing lens having a predetermined focal length f after the laser beam is incident on a diffuser having a predetermined diffusion angle θ, a core damage mode or a peripheral damage mode occurs. The graph of FIG. 15 is a graph in which energy, which is obtained when the core damage mode or the peripheral damage mode starts to occur, is plotted. An experimental method is the same as the method described with reference to FIG. 14. In FIG. 15, a solid line represents the damage threshold energy of an end face of the optical fiber that is estimated from the damage threshold energy density of a quartz core. Further, a dotted line represents the damage threshold energy of an air gap-optical fiber cable (FIG. 5) that includes a quartz core having a diameter of 400 µm and a fluorine-doped quartz clad having a thickness of 440 µm. Furthermore, a dashed-dotted line represents the damage threshold energy of a general optical fiber cable (that is, of which the side surface of the clad at an end portion is not exposed to the outside and in which an adhesive and a ferrule made of stainless steel are present up to the periphery of an end portion) that includes a quartz core having a diameter of 400 µm.

The behavior of the damage threshold energy of this graph shows that the damage mode of a general optical fiber cable is switched to a peripheral damage mode from a core damage mode at a beam diameter of about ½ of the diameter of the core as a boundary but the damage mode of an air gap-optical fiber cable is not switched to a peripheral damage mode even at a beam diameter of about ½ of the diameter of the core and a core damage mode is dominant up to a larger beam diameter. The reason for this is that the durability of the above-mentioned members, which are provided around the core, against a laser beam L is lower than that of the core made of quartz or the like.

That is, when the optical fiber cable 82 includes the light energy resistant structure at the light incident-side end portion thereof, the peripheral damage mode of an end face of the optical fiber cable 82 does not occur. Accordingly, an upper limit of the beam diameter D is not particularly limited in terms of the suppression of damage to the end face of the optical fiber cable 82. However, when the minimum beam diameter D is larger than the diameter $d_{in}$ of the core of the optical fiber 82a, damage to the periphery of the optical fiber 82a does not occur but a laser beam L spreads to the outside of the core 84a. For this reason, the transmission efficiency of energy is lowered. Accordingly, in terms of making a laser beam L be efficiently incident on the core 84a of the optical fiber 82a of the optical fiber cable 82, it is preferable that the upper limit of the beam diameter D be equal to or smaller than the diameter $d_{in}$ of the core 84a.

As described above, the light source unit and the photoacoustic measurement apparatus according to this embodiment transmit light to the connector receiving portion by using the optical fiber. Accordingly, even though the inside of the housing and the housing wall move in different manners with a temperature change and vibration, it is possible to prevent the incident position of light, which is incident on the connector receiving portion, from being shifted. In addition, the light source unit and the photoacoustic measurement apparatus according to the invention increase the distribution of a propagation angle of light flux, which is included in a laser beam, by allowing the laser beam to pass through the diffuser once, and control a beam diameter, which is obtained when the laser beam is incident on the optical fiber, by using the focal length of the condensing lens system. Accordingly, when condensing a laser beam by the condensing lens system and allowing the laser beam to be incident on the optical fiber, the light source unit and the photoacoustic measurement apparatus can prevent the laser beam from being excessively narrowed. Therefore, it is possible to prevent damage to the optical fiber that is caused when local light energy exceeds the damage threshold energy of the optical fiber. As a result, it is possible to more stably and efficiently transmit light in the housing of the light source unit.

<Design Changes>

Moreover, since the transmission of light in the unit housing 13b is performed by using the optical fiber in the invention, the structure of the connector hardly affects an optical path. Accordingly, there is also an advantage (third effect) of increasing the degree of freedom in design. As a result, for example, the following connector structure can be employed.

Figure 16A:
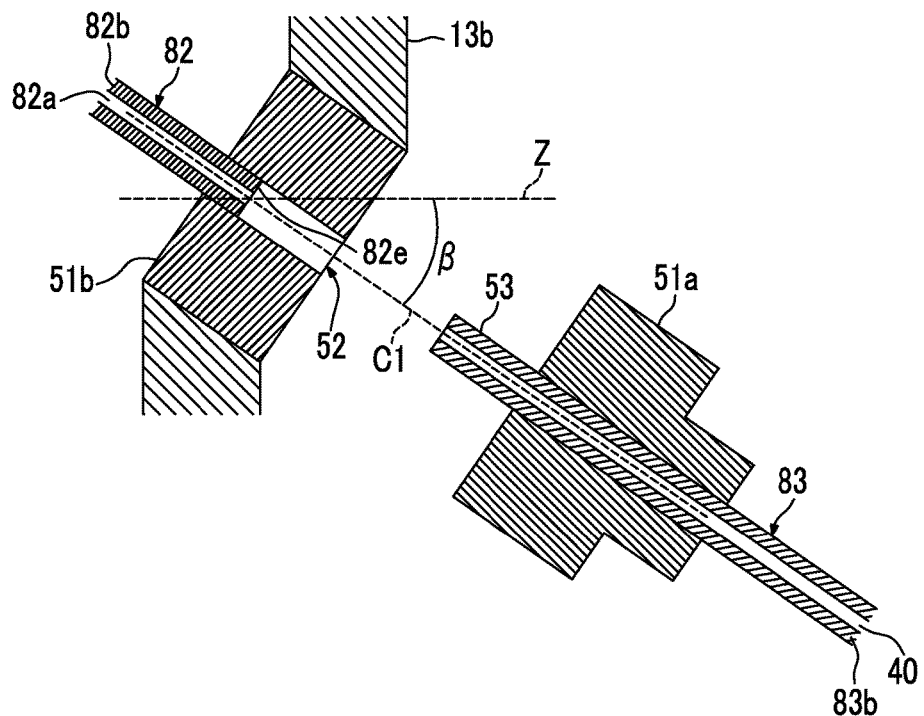
FIGS. 16A and 16B are schematic views showing another example of the structure of a connector.
Figure 16B:
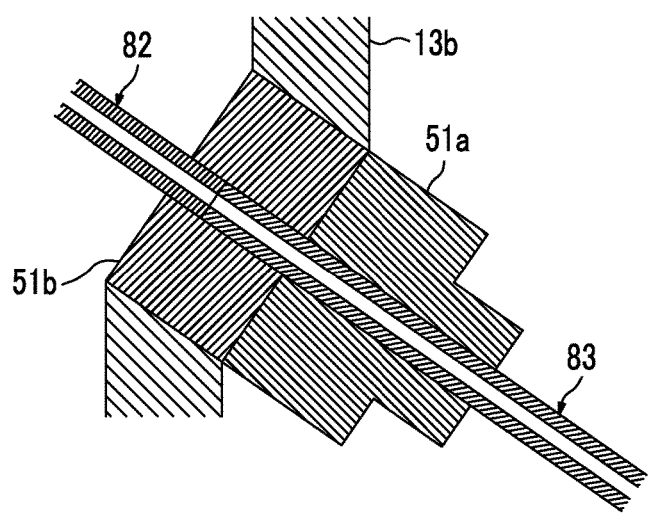

In a connector shown in FIGS. 16A and 16B, a receptacle 51b is provided in a unit housing 13b so that the direction of an optical axis C1 (first optical axis) of an optical fiber cable 82 (or an optical fiber 82a) on the light-emitting side has an inclination β. The receptacle 51b is provided with an insertion opening 52 into which an insertion portion 53 of a plug 51a is inserted. In FIGS. 16A and 16B, the insertion portion 53 includes an optical fiber 40 and a covering member 83b, that is, the insertion portion 53 is formed of an optical fiber cable 83. The insertion opening 52 has substantially the same diameter as the diameter of the optical fiber cable 82 (a total length of the optical fiber 82a and a covering member 82b), and the optical fiber cable 82 is fixed to the insertion opening 52. Further, since the receptacle 51b is obliquely installed in the unit housing 13b, the optical fiber cable 82 is fixed so that the direction of the optical axis C1 has the inclination β. "Having an inclination" means that the direction of the optical axis C1 has a downward angle from a horizontal. FIG. 16A is a schematic view showing a state in which the insertion portion 53 of the plug 51a is not yet inserted into the insertion opening 52 of the receptacle 51b, and FIG. 16B is a schematic view showing a state in which the insertion portion 53 of the plug 51a is inserted into the insertion opening 52 of the receptacle 51b. Meanwhile, fixing means for the plug 51a and the receptacle 51b is not shown in FIGS. 16A and 16B, but known means can be appropriately employed as the fixing means. According to this connector structure, it is possible to prevent a laser beam from being accidentally emitted horizontally to a space outside the unit housing 13b, and a laser beam reaches a floor, the ground, or the like and is absorbed even though a laser beam is emitted. Accordingly, safety is improved.

Figure 17A:
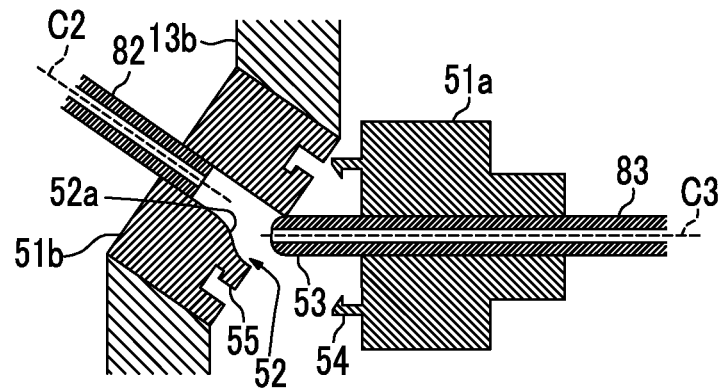
FIGS. 17A, 17B, and 17C are schematic views showing another example of the structure of the connector.
Figure 17B:
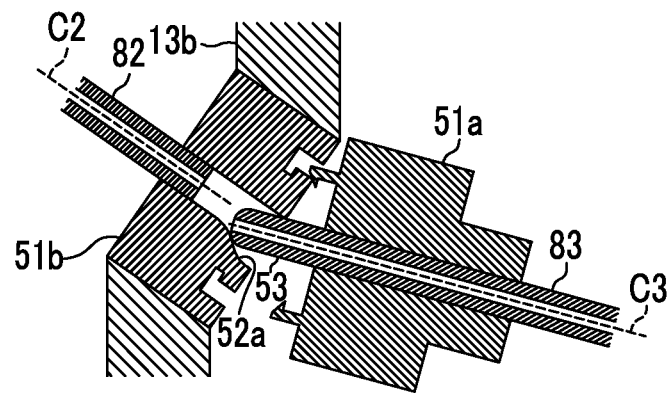
Figure 17C:
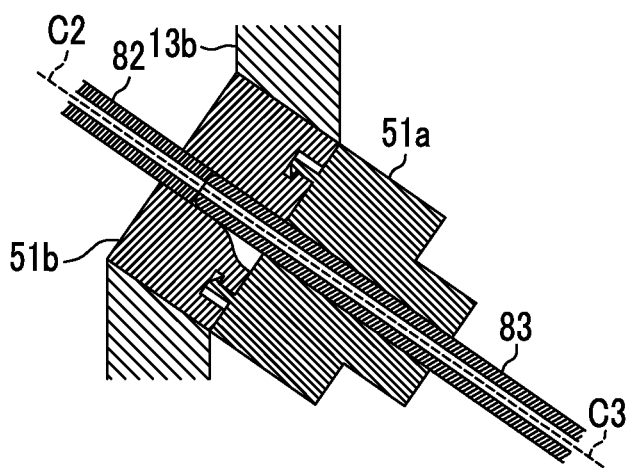

A connector structure shown in FIGS. 17A, 17B, and 17C is different from the connector structure of FIGS. 16A and 16B in terms of the fact that there is provided a guide structure in which an opening width of an insertion opening 52 is larger than the width of an inner portion of the insertion opening and an inner wall surface 52a is curved from the opening side toward the inner portion side, a fact that fixing means 54 and 55 are provided, and a fact that an end of the insertion portion 53 is rounded. "The guide structure is curved" means that the wall surface of at least a part of the insertion opening 52 only has to be curved in the cross-section of the insertion opening 52 taken along, for example, an arbitrary plane including an optical axis C2 of the optical fiber cable 82. Since the cross-section of the insertion opening 52 taken along a plane, which includes the optical axis C2 and is parallel to the plane of paper, is shown in FIGS. 17A, 17B, and 17C, it is understood that the wall surface 52a of the insertion opening 52 is curved. Since this guide structure is employed, the insertion portion 53 is smoothly guided (FIG. 17B) with the insertion of the insertion portion 53 so that an optical axis C3 (second optical axis) of the optical fiber cable 83 (or an optical fiber 40) on the light incident side corresponds to the optical axis C2 even when the insertion portion 53 is horizontally inserted as shown in, for example, FIG. 17A. Accordingly, the plug 51a and the receptacle 51b can be easily fitted to each other (FIG. 17C) in comparison with the case of the connector structure of FIGS. 16A and 16B. The reason why the end of the insertion portion 53 is rounded is to reduce resistance when the end of the insertion portion 53 slides on the wall surface 52a, and the round end of the insertion portion 53 is not essential. Further, in FIGS. 17A, 17B, and 17C, the connector structure includes a protrusion 54 and a recess 55 to be engaged with each other so that the plug 51a can be fitted to the receptacle 51b by only sliding on the receptacle 51b. Meanwhile, the fixing means is not limited to the protrusion 54 and the recess 55, and other known means, such as a push pin or a screw, can be employed as the fixing means.

Figure 18:
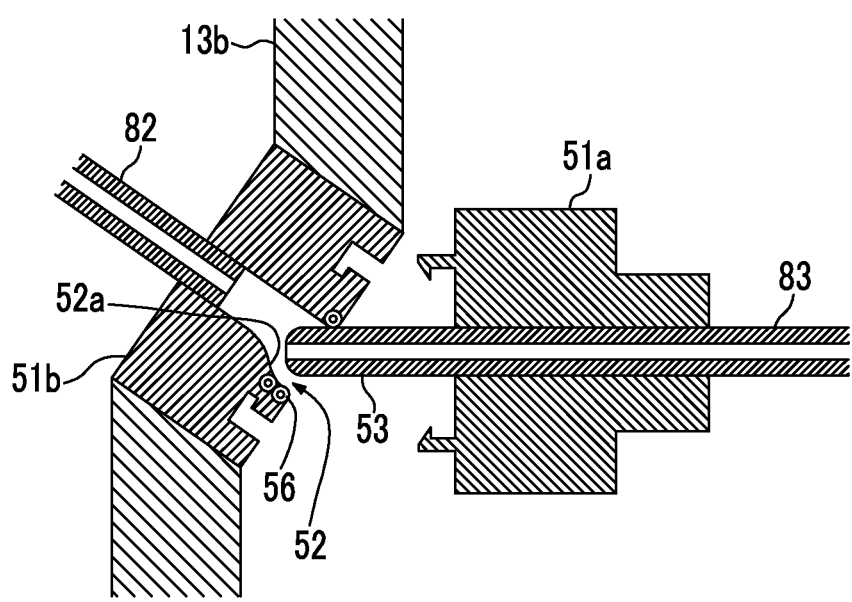
FIG. 18 is a schematic view showing another example of the structure of the connector.

A connector structure shown in FIG. 18 is different from the connector structure of FIGS. 17A, 17B, and 17C in terms of the fact that rollers 56 are installed at an opening portion of an insertion opening 52. Since this guide structure is employed, it is possible to further reduce resistance when the insertion portion 53 slides on the wall surface in the insertion opening 52. Accordingly, the plug 51a and the receptacle 51b can be easily fitted to each other in comparison with the case of the connector structure of FIGS. 17A, 17B, and 17C. The installation positions and the number of the rollers are not particularly limited, but it is preferable that the rollers be installed along the wall surface in the insertion opening 52 with which the insertion portion 53 is likely to come into contact.

[Second Embodiment]

Figure 19:
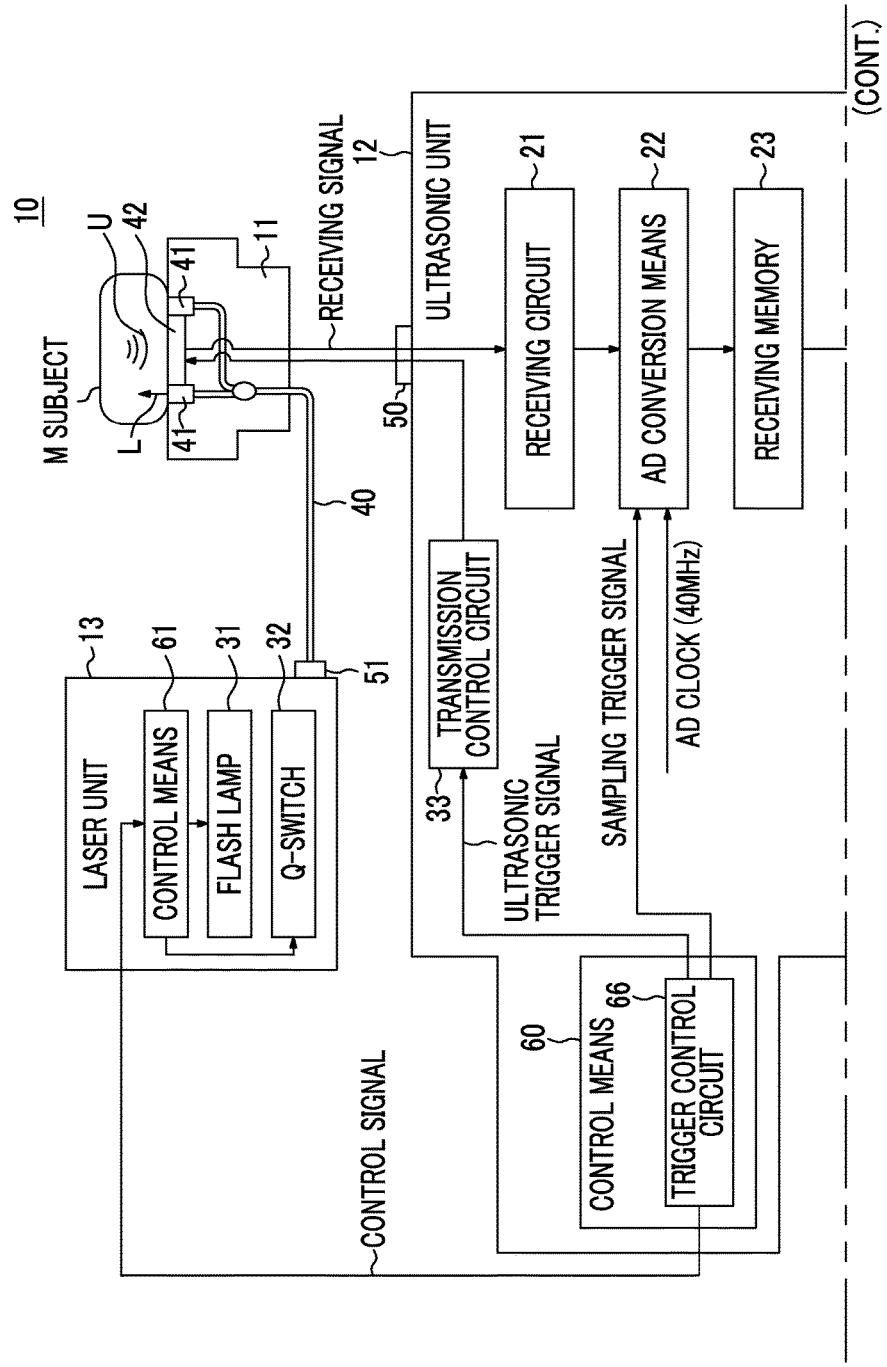
FIG. 19 is a block diagram showing the internal configuration of a photoacoustic measurement apparatus of a second embodiment.
Figure 20:
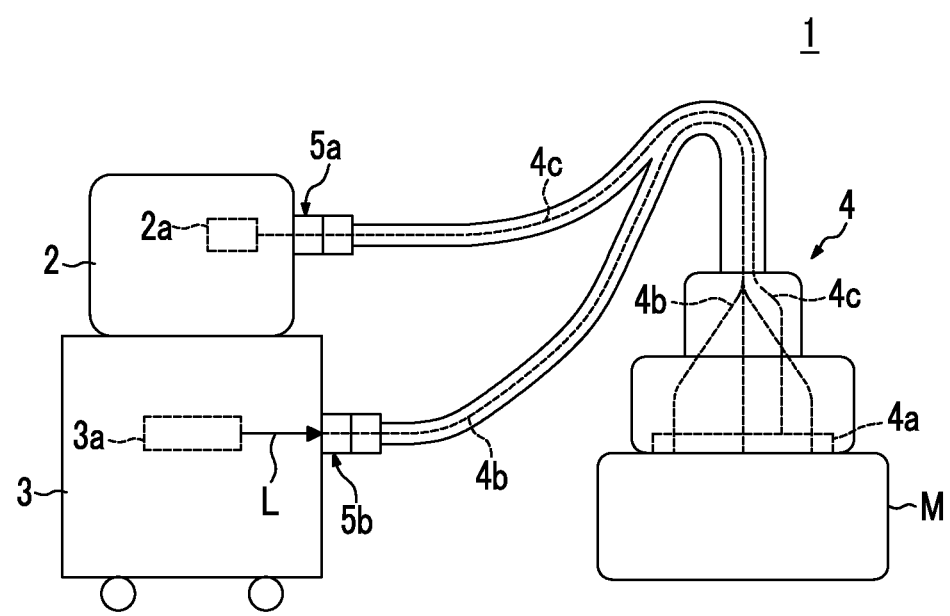
FIG. 20 is a schematic view showing the configuration of a photoacoustic measurement apparatus in the related art.

Next, a second embodiment of a photoacoustic measurement apparatus will be described. A case in which the photoacoustic measurement apparatus is a photoacoustic image forming apparatus 10 will be specifically described even in this embodiment. FIG. 19 is a block diagram showing the configuration of the photoacoustic image forming apparatus 10 of this embodiment. This embodiment is different from the first embodiment in terms of the fact that an ultrasonic image is also formed in addition to a photoacoustic image. Accordingly, the detailed description of the same components as the components of the first embodiment will be omitted unless particularly necessary.

As in the first embodiment, the photoacoustic image forming apparatus 10 of this embodiment includes a probe 11, an ultrasonic unit 12, a laser unit 13, image display means 14, and input means 16 according to the invention.

<Ultrasonic Unit>

The ultrasonic unit 12 of this embodiment includes a transmission control circuit 33, data separating means 34, ultrasonic image reconstruction means 35, detection/logarithmic conversion means 36, and ultrasonic image construction means 37 in addition to the configuration of the photoacoustic image forming apparatus shown in FIG. 3.

In this embodiment, the probe 11 not only detects a photoacoustic signal but also outputs (transmits) an ultrasonic wave to a subject and detects (receives) a reflected ultrasonic wave, which is reflected from the subject, of the ultrasonic wave that is transmitted to the subject. The above-mentioned acoustic detecting element array may be used as an acoustic detecting element that transmits and receives an ultrasonic wave, and a new acoustic detecting element array, which is separately provided in the probe 11 to transmit and receive an ultrasonic wave, may be used as an acoustic detecting element that transmits and receives an ultrasonic wave. Further, the transmission and reception of an ultrasonic wave may be separated from each other. For example, an ultrasonic wave may be transmitted from a position that is different from the position of the probe 11, and a reflected ultrasonic wave of the transmitted ultrasonic wave may be received by the probe 11.

The trigger control circuit 66 transmits an ultrasonic wave transmission trigger signal, which instructs the transmission control circuit 33 to transmit an ultrasonic wave, to the transmission control circuit 33 when an ultrasonic image is formed. When receiving this trigger signal, the transmission control circuit 33 allows an ultrasonic wave to be transmitted from the probe 11. After transmitting an ultrasonic wave, the probe 11 detects a reflected ultrasonic wave that is reflected from the subject.

The reflected ultrasonic wave, which is detected by the probe 11, is input to the AD conversion means 22 through the receiving circuit 21. The trigger control circuit 66 transmits a sampling trigger signal to the AD conversion means 22 in accordance with ultrasonic wave transmission timing, and starts the sampling of reflected ultrasonic waves. Here, the reflected ultrasonic wave travels back and forth between the probe 11 and a position from which the ultrasonic wave is reflected, but the photoacoustic signal merely travels to the probe 11 from a position from which the photoacoustic signal is generated. Since time required to detect a reflected ultrasonic wave is twice as long as time required to detect a photoacoustic signal generated from the same depth position, the sampling clock of the AD conversion means 22 may be a half of a sampling clock, which is obtained when photoacoustic signals are sampled, for example, 20 MHz. The AD conversion means 22 stores a sampling signal of a reflected ultrasonic wave in the receiving memory 23. Any one of the sampling of photoacoustic signals and the sampling of reflected ultrasonic waves may be performed first.

The data separating means 34 separates the sampling signals of the photoacoustic signals and the sampling signals of the reflected ultrasonic waves, which are stored in the receiving memory 23, from each other. The data separating means 34 inputs the separated sampling signals of the photoacoustic signals to the photoacoustic image reconstruction means 24. The formation of a photoacoustic image is the same as that in the first embodiment. Meanwhile, the data separating means 34 inputs the separated sampling signals of the reflected ultrasonic waves to the ultrasonic image reconstruction means 35.

The ultrasonic image reconstruction means 35 generates data of each line of the ultrasonic image on the basis of the reflected ultrasonic waves (the sampling signals of the reflected ultrasonic waves) that are detected by a plurality of acoustic detecting elements of the probe 11. A delay addition method or the like can be used for the generation of the data of each line as in the generation of data of each line that is performed by the photoacoustic image reconstruction means 24. The detection/logarithmic conversion means 36 obtains an envelope of data of each line output from the ultrasonic image reconstruction means 35, and logarithmically converts the envelope.

The ultrasonic image construction means 37 forms an ultrasonic image on the basis of the data of each line that has been subjected to logarithmic conversion.

The image synthesizing means 38 synthesizes a photoacoustic image and an ultrasonic image. The image synthesizing means 38 synthesizes an image by superimposing, for example, the photoacoustic image and the ultrasonic image. The synthesized image is displayed on the image display means 14. A photoacoustic image and an ultrasonic image may be displayed side by side on the image display means 14 without the synthesization of an image, or a photoacoustic image and an ultrasonic image can be displayed so as to be switched.

Since the photoacoustic measurement apparatus according to this embodiment also uses the light source unit of the invention as described above, the same effects as the effects of the first embodiment are obtained.

In addition, the photoacoustic measurement apparatus of this embodiment forms an ultrasonic image in addition to a photoacoustic image. Accordingly, it is possible to observe a portion that cannot be formed as an image in the photoacoustic image by referring to an ultrasonic image.

Meanwhile, a case in which the photoacoustic measurement apparatus forms a photoacoustic image or an ultrasonic image has been described above, but the formation of this image is not necessarily needed. For example, the photoacoustic measurement apparatus can also be adapted to measure only the presence/absence of an object to be measured, on the basis of the magnitude of a photoacoustic signal.

What is claimed is:

1. A light source unit that emits a laser beam to a light guide part of a probe, the light source unit comprising:
   a unit housing having a connector receiving portion detachably connected to a connector portion of the light guide part;
   a light source that is installed in the unit housing and outputs the laser beam;
   a diffusion part that diffuses the laser beam output from the light source;
   a condensing lens system that condenses the laser beam diffused by the diffusion part; and
   a light transmitting part that includes an optical fiber, which is a single fiber, transmitting the laser beam, which is condensed by the condensing lens system, to the connector receiving portion,
   wherein the connector receiving portion optically connects the optical fiber to the light guide part,
   wherein the diffusion part is an engineered diffuser or a holographic diffuser,
   the light transmitting part has a light energy resistant structure at a light incident-side end portion of the optical fiber,
   the condensing lens system condenses the laser beam so that a minimum beam diameter D of the laser beam defined by the following expression 1 is $d_{in}/2$ or more in a relationship between a diameter $d_{in}$ of a core of the optical fiber on a light incident side and the minimum beam diameter D, and
   a light incident-side end face of the core of the optical fiber is disposed so that the laser beam is incident on the light incident-side end face of the core while the diameter of the laser beam is $d_{in}/2$ or more, $$D = A \cdot f \cdot \tan\left(\sqrt{\left(\frac{\phi}{2}\right)^2 + \left(\frac{\theta}{2}\right)^2}\right) \quad \text{Expression 1}$$

in Expression 1, in a case in which the diffusion part is the engineered diffuser, A is 2.5 and in a case in which the diffusion part is the holographic diffuser, A is 2.4, f denotes a focal length of the condensing lens system, φ denotes a spread angle of the laser beam when the laser beam is incident on the diffusion part, and θ denotes a diffusion angle of the diffusion part.

2. The light source unit according to claim 1,
   wherein the light transmitting part is an air gap-optical fiber cable having a covering member that covers the optical fiber so that a side surface of the optical fiber adjacent to an end face of the optical fiber is exposed to the outside.

3. A light source unit that emits a laser beam to a light guide part of a probe, the light source unit comprising:
   a unit housing having a connector receiving portion detachably connected to a connector portion of the light guide part;
   a light source that is installed in the unit housing and outputs the laser beam,
   a diffusion part that diffuses the laser beam output from the light source;
   a condensing lens system that condenses the laser beam diffused by the diffusion part; and
   a light transmitting part that includes an optical fiber, which is a single fiber, transmitting the laser beam, which is condensed by the condensing lens system, to the connector receiving portion,
   wherein the connector receiving portion optically connects the optical fiber to the light guide part.,
   wherein the diffusion part is an engineered diffuser or a holographic diffuser,
   wherein the condensing lens system condenses the laser beam so that a minimum beam diameter D of the laser beam defined by the following expression 2 is in the range of $d_{in}/3$ to $2d_{in}/3$ in a relationship between a diameter $d_{in}$ of a core of the optical fiber on a light incident side and the minimum beam diameter D, and
   wherein a light incident-side end face of the core of the optical fiber is disposed so that the laser beam is incident on the light incident-side end face of the core while the diameter of the laser beam is in the range of $d_{in}/3$ to $2d_{in}/3$, $$D = A \cdot f \cdot \tan\left(\sqrt{\left(\frac{\phi}{2}\right)^2 + \left(\frac{\theta}{2}\right)^2}\right) \quad \text{Expression 2}$$

in Expression 2, in a case in which the diffusion part is the engineered diffuser, A is 2.5 and in a case in which the diffusion part is the holographic diffuser, A is 2.4, f denotes a focal length of the condensing lens system, φ denotes a spread angle of the laser beam when the laser beam is incident on the diffusion part, and θ denotes a diffusion angle of the diffusion part.

4. The light source unit according to claim 1, wherein the diffusion part makes a top of an energy profile of the incident laser beam flat.

5. The light source unit according to claim 3, wherein the diffusion part makes a top of an energy profile of the incident laser beam flat.

* * * * *